(12) United States Patent
Docherty et al.

(10) Patent No.: US 12,397,042 B2
(45) Date of Patent: *Aug. 26, 2025

(54) COMPOSITIONS AND METHODS FOR TREATING DIABETES

(71) Applicant: POVIVA CORP, Carson City, NV (US)

(72) Inventors: John Docherty, Port Perry (CA); Christopher Andrew Bunka, Kelowna (CA)

(73) Assignee: POVIVA CORP, Kelowna (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/967,259

(22) Filed: Dec. 3, 2024

(65) Prior Publication Data

US 2025/0177489 A1 Jun. 5, 2025

Related U.S. Application Data

(60) Provisional application No. 63/622,696, filed on Jan. 19, 2024, provisional application No. 63/617,759, filed on Jan. 4, 2024, provisional application No. 63/605,701, filed on Dec. 4, 2023.

(51) Int. Cl.
| | |
|---|---|
| *A61K 38/26* | (2006.01) |
| *A61K 9/48* | (2006.01) |
| *A61K 47/02* | (2006.01) |
| *A61K 47/26* | (2006.01) |
| *A61K 47/28* | (2006.01) |
| *A61K 47/44* | (2017.01) |
| *A61P 3/10* | (2006.01) |

(52) U.S. Cl.
CPC .............. *A61K 38/26* (2013.01); *A61K 9/485* (2013.01); *A61K 9/4858* (2013.01); *A61K 9/4875* (2013.01); *A61K 47/02* (2013.01); *A61K 47/26* (2013.01); *A61K 47/28* (2013.01); *A61K 47/44* (2013.01); *A61P 3/10* (2018.01)

(58) Field of Classification Search
CPC ........ A61K 38/26; A61K 47/28; A61K 47/44; A61K 47/26
See application file for complete search history.

(56) References Cited

U.S. PATENT DOCUMENTS

| | | |
|---|---|---|
| 2018/0235888 A1 | 8/2018 | Jensen et al. |
| 2018/0271792 A1 | 9/2018 | Mantripragada et al. |

OTHER PUBLICATIONS

Office Action U.S. Appl. No. 18/967,455 (co-0ending Application) dated Apr. 2, 2025.
U.S. Appl. No. 18/967,455, Response to Final Office Action, dated May 28, 2025.

*Primary Examiner* — Gyan Chandra
(74) *Attorney, Agent, or Firm* — FisherBroyles LLP; Anthony J DoVale

(57) ABSTRACT

Disclosed herein are compositions and methods for treating diabetes wherein the compositions comprise GLP-1 agonists. The disclosed compositions are also effective for reducing body weight and improving triglyceride and cholesterol levels. Disclosed herein are methods for treating type-2 diabetes in a subject, for lowering a subject's A1C, for lowering the body mass of a subject, and for regulating the incretin hormone levels of a subject.

11 Claims, 2 Drawing Sheets

COMPOSITIONS AND METHODS FOR TREATING DIABETES

FIELD

Disclosed herein are compositions and methods for treating diabetes wherein the compositions comprise GLP-1 agonists. The disclosed compositions are also effective for reducing body weight and improving triglyceride and cholesterol levels. Disclosed herein are methods for treating type-2 diabetes in a subject, for lowering a subject's A1C, for lowering the body mass of a subject, and for regulating the incretin hormone levels of a subject.

DETAILED DESCRIPTION OF THE DISCLOSURE

Figure 1:
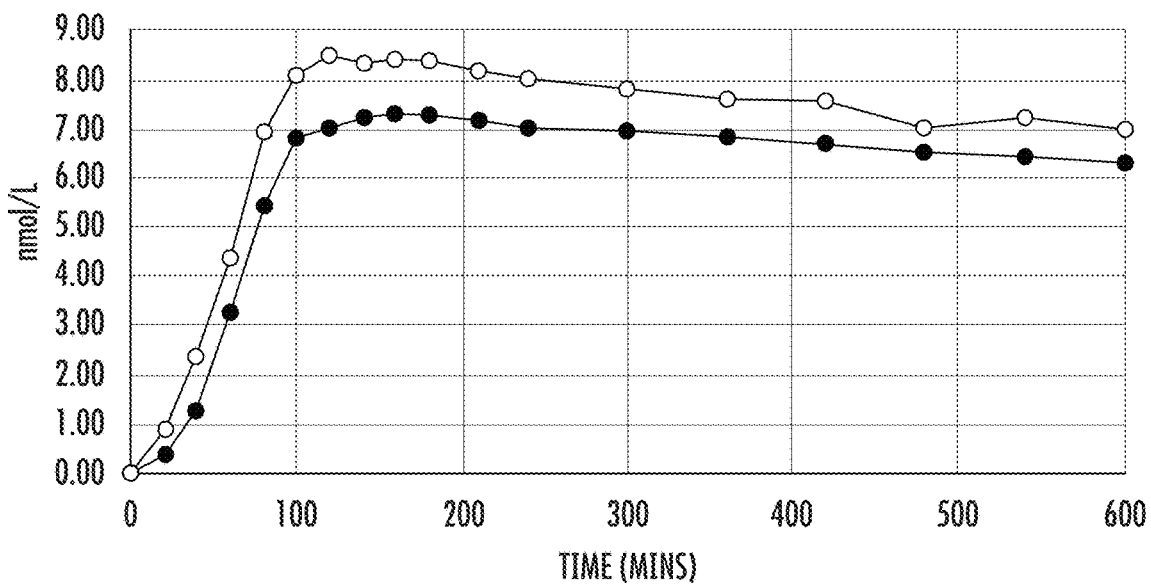
FIG. 1 is a plot of the semaglutide levels in nmol/L of the control subjects given a Rybelsus™ 7 mg tablet (●) versus the study subjects given the composition of Table 1 times 4 (○).

The materials, compounds, compositions, articles, and methods described herein can be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

As used herein, the term "subject" refers to a human or an animal that would benefit from being administered with the disclosed compositions described in the present application, such as those suffering from, without limitation one or more forms of diabetes.

As used herein, the terms "treat," "treating," "treatment," and the like refer to reducing or ameliorating a disorder and/or symptoms associated therewith. It will be appreciated that, although not precluded, treating epilepsy does not require that the diabetes, condition or symptoms associated diabetes be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant a material that is not biologically or otherwise undesirable, for example, the material can be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

The feature or features of one embodiment can be applied to other embodiments, even though not described or illustrated, unless expressly prohibited by this disclosure or the nature of the embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

Compositions

Incretin hormones are gut peptides that are secreted after nutrient intake and stimulate insulin secretion together with hyperglycemia. Glucagon-like peptide-1 (GLP-1) is a known incretin hormone found in the lower GI tract. Together with glucose-dependent insulinotropic polypeptide (GIP), they are responsible for the incretin effect: a two- to three-fold higher insulin secretory response to oral glucose as compared to intravenous glucose administration. In subjects with type 2 diabetes, this incretin effect is diminished or no longer present. Therefore, the administration of GLP-1 agonists provides a method for increasing the incretin response in type-2 diabetics.

Without wishing to be limited by theory it has been found that pharmacological stimulation of GLP-1 receptors significantly reduces plasma glucose and improves glycemic control. Thus, it has become a goal of incretin-based glucose-lowering medications to stimulate the activity of GLP-1 via pharmacological agonism.

Increase in GLP-1 activity results in a reduction in appetite and food intake, leading to weight loss in the long term. Since GLP-1 secretion from the gut seems to be impaired in obese subjects, this can even indicate a role in the pathophysiology of obesity. Along these lines, an increased secretion of GLP-1 induced by delivering nutrients to lower parts of the small intestines (rich in L cells) can be one factor explaining weight loss and improvements in glycemic control after bariatric surgery (e.g., Roux-en-Y gastric bypass).

Currently there are a number of peptide-based GLP-1 agonists marketed for use in controlling diabetes and weight loss, inter alia, dulaglutide (Trulicity™), exenatide (Byetta™), exenatide Extended Release (Bydureon BCise™), liraglutide (Victoza™), lixisenatide (Adlyxin™), semaglutide subcutaneous (Ozempic™), semaglutide tablet (RybelsusIM), and tirzepatide (Mounjaro™, Zepbound™). All of these GLP-1 agonists have to be administered via injection; all but semaglutide-containing tablets marketed under the tradename Rybelsus™.

Disclosed herein are compositions and methods for oral delivery of peptide-based GLP-1 inhibitors, thereby eliminating the need for delivery of these drugs by injection and alleviation of any injection site side effects. Oral delivery of these GLP-1 agonists also increases the level of compliance by the subject being treated.

The disclosed compositions comprise one or more GLP-1 agonists. These GLP-1 agonists increase the secretion of GLP-1 that is released in the gastrointestinal tract in response to eating. One role of GLP-1 is to prompt the body to produce more insulin, which reduces blood glucose (sugar). One significant result of this is a method for treating diabetes. Another is a method of reducing body mass (weight loss).

The disclosed compositions below are free flowing solids which contain no water. If moisture is present, it is an artifact of the process for preparing the compositions and would be less than 0.01% by weight of the composition. In one aspect, the amount of moisture is less than 0.001% by weight of the composition.

Compositions

Disclosed herein are compositions for treating type-2 diabetes in a subject, for lowering a subject's A1C, for lowering the body mass of a subject, and for regulating the incretin hormone levels of a subject, comprising:
   a) one or more GLP-1 agonists;
   b) one or more edible oils; and
   c) one or more adjunct ingredients and carriers.

One aspect of the disclosed compositions, comprise:
   a) from about 0.5% to about 20% by weight of one or more GLP-1 agonists;
   b) from about 0.5% to about 40% by weight of one or more edible oils;
   c) from about 0.01% to about 65% by weight of a bile salt extract;
   d) from about 35% to about 65% by weight of sodium bicarbonate; and
   e) from about 15% to about 85% by weight of one or more carriers.

In one embodiment of this aspect the compositions, comprise:
   a) from about 0.5% to about 20% by weight of one or more GLP-1 agonists chosen from dulaglutide, exenatide, liraglutide, lixisenatide, semaglutide, tirzepatide, or mixtures thereof;
   b) from about 0.5% to about 40% by weight of one or more edible oils chosen from olive oil, sunflower oil, coconut oil, canola oil, palm oil, soybean oil, corn oil, safflower oil, peanut oil, or mixtures thereof;
   c) from about 0.01% to about 65% by weight of a bile salt extract wherein the bile salt extract contains from about 45% to about 55% by weight of a bile salt selected from the group consisting of cholic acid, deoxycholic acid, taurocholate, glycocholic acid, or a mixture thereof;
   d) from about 35% to about 65% by weight of sodium bicarbonate; and
   e) from about 15% to about 85% by weight of one or more carriers.

In one iteration of this embodiment of this aspect the compositions, comprise:
   a) from about 0.5% to about 20% by weight of one or more GLP-1 agonists chosen from dulaglutide, exenatide, liraglutide, lixisenatide, semaglutide, tirzepatide, or mixtures thereof;
   b) from about 0.5% to about 40% by weight of one or more edible oils chosen from olive oil, sunflower oil, coconut oil, canola oil, palm oil, soybean oil, corn oil, safflower oil, peanut oil, or mixtures thereof;
   c) from about 0.01% to about 65% by weight of a bile salt extract wherein the bile salt extract contains from about 45% to about 55% by weight of a bile salt selected from the group consisting of cholic acid, deoxycholic acid, taurocholate, glycocholic acid, or mixtures thereof;
   d) from about 35% to about 65% by weight of sodium bicarbonate; and
   e) from about 15% to about 85% by weight of one or more carriers chosen from gum Arabic, inulin, mannitol, silicon dioxide, colloidal silicon dioxide, microcrystalline cellulose, D-lactose monohydrate, tapioca starch, tapioca flour, quillaia, or mixtures thereof.

In another iteration of this embodiment of this aspect the compositions, comprise:

a) from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of olive oil;
c) from about 0.01% to about 65% by weight of a bile salt extract wherein the bile salt extract contains from about 45% to about 55% by weight of a bile salt selected from the group consisting of cholic acid, deoxycholic acid, taurocholate, glycocholic acid, or mixtures thereof;
d) from about 35% to about 65% by weight of sodium bicarbonate; and
e) from about 15% to about 85% by weight of one or more carriers chosen from sodium N-[8-(2-hydroxybenzoyl) amino]caprylate (SNAC) or derivatives thereof, gum Arabic, inulin, mannitol, silicon dioxide, colloidal silicon dioxide, microcrystalline cellulose, D-lactose monohydrate, tapioca starch, tapioca flour, quillaia, or mixtures thereof.

In a further iteration of this embodiment of this aspect the compositions, comprise:
a) from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of olive oil;
c) from about 0.01% to about 65% by weight of deoxycholic acid;
d) from about 35% to about 65% by weight of sodium bicarbonate; and
e) from about 15% to about 85% by weight of one or more carriers chosen from sodium N-[8-(2-hydroxybenzoyl) amino]caprylate (SNAC), gum Arabic, inulin, mannitol, silicon dioxide, colloidal silicon dioxide, microcrystalline cellulose, D-lactose monohydrate, tapioca starch, tapioca flour, quillaia, or mixtures thereof.

In another iteration of this embodiment of this aspect the compositions, comprise:
a) from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of olive oil;
c) from about 0.01% to about 65% by weight deoxycholic acid;
d) from about 35% to about 65% by weight of sodium bicarbonate; and
e) from about 15% to about 85% by weight of one or more carriers chosen from gum Arabic, colloidal silicon dioxide, mannitol, or mixtures thereof.

In one non-limiting example of this iteration of this embodiment of this aspect the compositions, comprise:
a) from about 0.5% to about 20% by weight of semaglutide;
b) from about 0.5% to about 40% by weight of olive oil;
c) from about 0.01% to about 65% by weight deoxycholic acid;
d) from about 35% to about 65% by weight of sodium bicarbonate; and
e) from about 15% to about 85% by weight of gum Arabic, colloidal silicon dioxide, for example, Aeroperl™ 3000, mannitol, for example, Parteck™ M 100, and mixtures thereof.

Another aspect of the disclosed compositions comprise:
a) from about 0.5% to about 5% by weight of one or more GLP-1 agonists;
b) from about 0.5% to about 10% by weight of olive oil;
c) from about 0.01% to about 2% by weight deoxycholic acid;
d) from about 35% to about 65% by weight of sodium bicarbonate; and
e) from about 30% to about 60% by weight of gum Arabic, colloidal silicon dioxide, for example, Aeroperl™ 3000, mannitol, for example, Parteck™ M 100, and mixtures thereof.

In one embodiment of this aspect the disclosed compositions comprise:
a) from about 0.5% to about 5% by weight of semaglutide;
b) from about 0.5% to about 15% by weight of olive oil;
c) from about 0.01% to about 2% by weight deoxycholic acid;
d) from about 35% to about 65% by weight of sodium bicarbonate; and
e) from about 30% to about 60% by weight of colloidal silicon dioxide, for example, Aeroperl™ 3000, mannitol, for example, Parteck™ M 100, or mixtures thereof.

In one iteration of this embodiment the compositions comprise:
a) from about 0.5% to about 5% by weight of semaglutide;
b) from about 0.5% to about 10% by weight of olive oil;
c) from about 0.01% to about 2% by weight deoxycholic acid;
d) from about 35% to about 65% by weight of sodium bicarbonate; and
e) from about 30% to about 60% by weight of colloidal silicon dioxide, mannitol, or mixtures thereof.

In another iteration of this embodiment the compositions comprise:
a) from about 0.5% to about 5% by weight of semaglutide;
b) from about 0.5% to about 10% by weight of olive oil;
c) from about 0.01% to about 5% by weight deoxycholic acid;
d) from about 35% to about 65% by weight of sodium bicarbonate; and
e) from about 30% to about 60% by weight of colloidal silicon dioxide.

In a further iteration of this embodiment the compositions comprise:
a) from about 0.5% to about 5% by weight of semaglutide;
b) from about 0.5% to about 10% by weight of olive oil;
c) from about 0.01% to about 5% by weight deoxycholic acid;
d) from about 35% to about 65% by weight of sodium bicarbonate; and
e) from about 30% to about 60% by weight of mannitol.

In another embodiment of this aspect the disclosed compositions comprise:
a) from about 0.5% to about 5% by weight of liraglutide;
b) from about 0.5% to about 15% by weight of olive oil;
c) from about 0.01% to about 2% by weight deoxycholic acid;
d) from about 35% to about 65% by weight of sodium bicarbonate; and
e) from about 30% to about 60% by weight of gum Arabic, colloidal silicon dioxide, for example, Aeroperl™ 3000, mannitol, for example, Parteck™ M 100, or mixtures thereof.

In one iteration of this embodiment the compositions comprise:
- a) from about 0.5% to about 5% by weight of liraglutide;
- b) from about 0.5% to about 10% by weight of olive oil;
- c) from about 0.01% to about 2% by weight deoxycholic acid;
- d) from about 35% to about 65% by weight of sodium bicarbonate; and
- e) from about 30% to about 60% by weight of colloidal silicon dioxide, mannitol, or mixtures thereof.

In another iteration of this embodiment the compositions comprise:
- a) from about 0.5% to about 5% by weight of liraglutide;
- b) from about 0.5% to about 10% by weight of olive oil;
- c) from about 0.01% to about 5% by weight deoxycholic acid;
- d) from about 35% to about 65% by weight of sodium bicarbonate; and
- e) from about 30% to about 60% by weight of colloidal silicon dioxide.

In a further iteration of this embodiment the compositions comprise:
- a) from about 0.5% to about 5% by weight of liraglutide;
- b) from about 0.5% to about 10% by weight of olive oil;
- c) from about 0.01% to about 5% by weight deoxycholic acid;
- d) from about 35% to about 65% by weight of sodium bicarbonate; and
- e) from about 30% to about 60% by weight of mannitol.

The disclosed compositions can comprise from about 0.5% to about 20% by weight of one or more GLP-1 agonists. Non-limiting examples of GLP-1 agonists include dulaglutide, exenatide, liraglutide, lixisenatide, semaglutide, and tirzepatide. In one embodiment the compositions can comprise from about 1% to about 10% by weight of one or more GLP-1 agonists. In a further embodiment the compositions comprise from about 0.5% to about 5% by weight of one or more GLP-1 agonists. In another embodiment the compositions comprise from about 1% to about 7% by weight of one or more GLP-1 agonists. In a yet further embodiment the compositions comprise from about 3.5% to about 10% by weight of one or more GLP-1 agonists. In a yet still further embodiment the compositions comprise from about 1% to about 5% by weight of one or more GLP-1 agonists.

The disclosed compositions can comprise from about 0.5% to about 20% by weight of one or more GLP-1 agonists, for example, 0.5%, 0.6%, 0.7%. 0.8%, 0.9%, 1%, 2%, 3%, 4%, 5%, 6%, 7%, 8%, 9%, 10%, 11%, 12%, 13%, 14%, 15%, 16%, 17%, 18, 19%, or 20%, or any fractional part thereof, for example, 1.27%, 1.96%, and 2.25%.

The disclosed compositions can comprise from about 0.5% to about 40% by weight of one or more edible oils chosen from olive oil, sunflower oil, coconut oil, canola oil, palm oil, soybean oil, corn oil, safflower oil, peanut oil, or mixtures thereof. In one embodiment the compositions can comprise from about 5% to about 25% by weight of one or more edible oils. In another embodiment the compositions can comprise from about 5% to about 20% by weight of one or more edible oils. In further embodiment the compositions can comprise from about 10% to about 25% by weight of one or more edible oils. In a still further embodiment the compositions can comprise from about 0.5% to about 15% by weight of one or more edible oils. In a yet further embodiment the compositions can comprise from about 1% to about 10% by weight of one or more edible oils. In still yet further embodiment the compositions can comprise from about 0.5% to about 10% by weight of one or more edible oils.

The disclosed compositions can comprise from about 0.5% to about 40% by weight of one or more edible oils chosen from olive oil, sunflower oil, coconut oil, canola oil, palm oil, soybean oil, corn oil, safflower oil, peanut oil, or mixtures thereof, for example, 0.5%, 0.6%, 0.7%, 0.8%. 0.9%, 1%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.1%, 4.15%, 4.2%, 4.25%, 4.3%, 4.35%, 4.4%, 4.45%, 4.5%, 4.55%, 4.6%, 4.65%, 4.7%, 4.75%, 4.8%, 4.85%, 4.9%, 4.95%, 5%, 5.1%, 5.15%, 5.2%, 5.25%, 5.3%, 5.35%, 5.4%, 5.45%, 5.5%, 5.55%, 5.6%, 5.65%, 5.7%, 5.75%, 5.8%, 5.85%, 5.9%, 5.95%, 6%, 6.1%, 6.15%, 6.2%, 6.25%, 6.3%, 6.35%, 6.4%, 6.45%, 6.5%, 6.55%, 6.6%, 6.65%, 6.7%, 6.75%, 6.8%, 6.85%, 6.9%, 6.95%, 7%, 7.1%, 7.15%, 7.2%, 7.25%, 7.3%, 7.35%, 7.4%, 7.45%, 7.5%, 7.55%, 7.6%, 7.65%, 7.7%, 7.75%, 7.8%, 7.85%, 7.9%, 7.95%, 8%, 8.1%, 8.15%, 8.2%, 8.25%, 8.3%, 8.35%, 8.4%, 8.45%, 8.5%, 8.55%, 8.6%, 8.65%, 8.7%, 8.75%, 8.8%, 8.85%, 8.9%, 8.95%, 9%, 9.1%, 9.15%, 9.2%, 9.25%, 9.3%, 9.35%, 9.4%, 9.45%, 9.5%, 9.55%, 9.6%, 9.65%, 9.7%, 9.75%, 9.8%, 9.85%, 9.9%, 9.95%, or 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, or any fractional part thereof.

The ratio of the one or more GLP-1 agonists to the one or more edible oils is from about 1:1 to about 1:10, for example, 1:1, 1:2, 1:3, 1:4, 1:5, 1:6, 1:7, 1:8, 1:9, or 1:10, or any fractional amount thereof, for example, 1:1.5, 1:4.2, or 1:8.6. In one embodiment the ratio of the one or more GLP-1 agonist to the one or more edible oils is 1:1. In another embodiment the ratio of the one or more GLP-1 agonist to the one or more edible oils is 1:2. In a further embodiment the ratio of the one or more GLP-1 agonist to the one or more edible oils is 1:3.

The following are non-limiting examples of the disclosed compositions.

TABLE A

| Ingredients (%) | 1 | 2 | 3 | 4 | 5 |
| --- | --- | --- | --- | --- | --- |
| semaglutide | 1.5 | 1.5 | 2 | 2.2 | 2.5 |
| olive oil | 3 | 4.5 | 4 | 4.4 | 5 |
| Aeroperl ™ 300 | 26.2 | 25.8 | 25.1 | 25.36 | 24.8 |
| Parteck ™ M 100 | 25.3 | 24.8 | 23.45 | 22.2 | 22 |
| Deoxycholic acid | 0.5 | 0.4 | 0.45 | 0.44 | 0.52 |
| Sodium bicarbonate | 43.5 | 43.0 | 45 | 45.4 | 45.18 |
| total | 100 | 100 | 100 | 100 | 100 |

TABLE B

| Ingredients (%) | 6 | 7 | 8 | 9 | 10 |
| --- | --- | --- | --- | --- | --- |
| liraglutide | 1.5 | 1.5 | 2 | 2.2 | 2.5 |
| olive oil | 3 | 4.5 | 4 | 4.4 | 5 |
| Aeroperl ™ 300 | 26.2 | 25.8 | 25.1 | 25.36 | 24.8 |
| Parteck ™ M 100 | 25.3 | 24.8 | 23.45 | 22.2 | 22 |

TABLE B-continued

| Ingredients (%) | 6 | 7 | 8 | 9 | 10 |
|---|---|---|---|---|---|
| Deoxycholic acid | 0.5 | 0.4 | 0.45 | 0.44 | 0.52 |
| Sodium bicarbonate | 43.5 | 43.0 | 45 | 45.4 | 45.18 |
| total | 100 | 100 | 100 | 100 | 100 |

In a further aspect of the present disclosure the compositions comprise:
a) from about 0.01 mg to about 50 mg of one or more GLP-1 agonists chosen from dulaglutide, exenatide, liraglutide, lixisenatide, semaglutide, tirzepatide, or mixtures thereof;
b) from about 0.01 mg to about 100 mg of one or more edible oils;
c) from about 0.005 mg to about 250 mg of a bile salt extract;
d) from about 20 mg to about 250 mg of sodium bicarbonate; and
e) from about 0.5 mg to about 400 mg of one or more carriers.

In one embodiment of this aspect of the present disclosure the compositions comprise:
a) from about 0.1 mg to about 50 mg of one or more GLP-1 agonists chosen from dulaglutide, exenatide, liraglutide, lixisenatide, semaglutide, tirzepatide, or mixtures thereof;
b) from about 0.1 mg to about 100 mg of one or more edible oils chosen from olive oil, sunflower oil, coconut oil, canola oil, palm oil, soybean oil, corn oil, safflower oil, peanut oil, or mixtures thereof;
c) from about 0.01 mg to about 250 mg of a bile salt extract wherein the bile salts are an extract containing from about 45% to about 55% by weight of cholic acid, deoxycholic acid, taurocholate, glycocholic acid, and mixtures thereof;
d) from about 20 mg to about 250 mg of sodium bicarbonate; and
e) from about 10 mg to about 50 mg of one or more carriers.

In one iteration of this embodiment of this aspect of the present disclosure the compositions comprise:
a) from about 0.1 mg to about 50 mg of one or more GLP-1 agonists chosen from dulaglutide, exenatide, liraglutide, lixisenatide, semaglutide, tirzepatide, or mixtures thereof;
b) from about 0.1 mg to about 100 mg of one or more edible oils chosen from olive oil, sunflower oil, coconut oil, canola oil, palm oil, soybean oil, corn oil, safflower oil, peanut oil, or mixtures thereof;
c) from about 0.1 mg to about 250 mg of a bile salt extract wherein the bile salts are an extract containing from about 45% to about 55% by weight of cholic acid, deoxycholic acid, taurocholate, glycocholic acid, and mixtures thereof;
d) from about 20 mg to about 250 mg of sodium bicarbonate; and
e) from about 10 mg to about 50 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In another aspect of the present disclosure the compositions comprise:
a) from about 0.01 mg to about 2 mg of one or more GLP-1 agonists chosen from dulaglutide, exenatide, liraglutide, lixisenatide, semaglutide, tirzepatide, or mixtures thereof;
b) from about 0.01 mg to about 4 mg of one or more edible oils chosen from olive oil, sunflower oil, coconut oil, canola oil, palm oil, soybean oil, corn oil, safflower oil, peanut oil, or mixtures thereof;
c) from about 0.005 mg to about 0.5 mg of a bile salt extract wherein the bile salts are an extract containing from about 45% to about 55% by weight of cholic acid, deoxycholic acid, taurocholate, glycocholic acid, and mixtures thereof;
d) from about 0.5 mg to about 10 mg of sodium bicarbonate; and
e) from about 1 mg to about 10 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one embodiment of this aspect of the present disclosure the compositions comprise:
a) from about 0.01 mg to about 2 mg of one or more GLP-1 agonists chosen from dulaglutide, exenatide, liraglutide, lixisenatide, semaglutide, tirzepatide, or mixtures thereof;
b) from about 0.01 mg to about 4 mg of olive oil;
c) from about 0.005 mg to about 0.5 mg of a bile salt extract wherein the bile salts are an extract containing from about 45% to about 55% by weight of cholic acid, deoxycholic acid, taurocholate, glycocholic acid, and mixtures thereof;
d) from about 0.5 mg to about 10 mg of sodium bicarbonate; and
e) from about 1 mg to about 10 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this embodiment of this aspect of the present disclosure the compositions comprise:
a) from about 0.01 mg to about 2 mg of one or more GLP-1 agonists chosen from dulaglutide, exenatide, liraglutide, lixisenatide, semaglutide, tirzepatide, or mixtures thereof;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In another iteration of this embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and e) from about 1 mg to about 10 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one embodiment of this aspect of the present disclosure the compositions comprise:
a) from about 0.01 mg to about 2 mg of one or more GLP-1 agonists chosen from dulaglutide, exenatide, liraglutide, lixisenatide, semaglutide, tirzepatide, or mixtures thereof;
b) from about 0.01 mg to about 4 mg of one or more edible oils chosen from olive oil, sunflower oil, coconut oil, canola oil, palm oil, soybean oil, corn oil, safflower oil, peanut oil, or mixtures thereof;
c) from about 0.005 mg to about 0.5 mg of a bile salt extract wherein the bile salts are an extract containing from about 45% to about 55% by weight of cholic acid, deoxycholic acid, taurocholate, glycocholic acid, and mixtures thereof;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In one iteration of this embodiment of this aspect of the present disclosure the compositions comprise:
a) from about 0.01 mg to about 2 mg of one or more GLP-1 agonists chosen from liraglutide, semaglutide, or mixtures thereof;
b) from about 0.01 mg to about 4 mg of one or more edible oils chosen from olive oil, sunflower oil, coconut oil, canola oil, palm oil, soybean oil, corn oil, safflower oil, peanut oil, or mixtures thereof;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In another iteration of this embodiment of this aspect of the present disclosure the compositions comprise:
a) from about 0.01 mg to about 2 mg of one or more GLP-1 agonists chosen from liraglutide, semaglutide, or mixtures thereof;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In a further iteration of this embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In a still further iteration of this embodiment of this aspect of the present disclosure the compositions comprise:
a) from about 0.01 mg to about 2 mg of liraglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In one embodiment of this aspect of the present disclosure the compositions comprise:
a) from about 0.01 mg to about 2 mg of semaglutide;
b) from about 0.01 mg to about 4 mg of one or more edible oils chosen from olive oil, sunflower oil, coconut oil, canola oil, palm oil, soybean oil, corn oil, safflower oil, peanut oil, or mixtures thereof;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In another iteration of this embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In a further iteration of this embodiment of this aspect of the present disclosure the compositions comprise:
a) from about 0.01 mg to about 2 mg of semaglutide;
b) from about 0.01 mg to about 4 mg of sunflower oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In another iteration of this embodiment of this aspect of the present disclosure the compositions comprise:

a) from about 0.01 mg to about 2 mg of liraglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In a further iteration of this embodiment of this aspect of the present disclosure the compositions comprise:
a) from about 0.01 mg to about 2 mg of liraglutide;
b) from about 0.01 mg to about 4 mg of sunflower oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from mannitol, silicon dioxide, colloidal silicon dioxide, or mixtures thereof.

In one embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of one or more carriers chosen mannitol, colloidal silicon dioxide, or mixtures thereof.

In a further iteration of this embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of mannitol.

In another iteration of this embodiment of this aspect of the present disclosure the compositions comprise:
a) from about 0.01 mg to about 2 mg of semaglutide;
b) from about 0.01 mg to about 4 mg of olive oil;
c) from about 0.005 mg to about 0.5 mg of deoxycholic acid;
d) from about 0.5 mg to about 10 mg of sodium bicarbonate; and
e) from about 1 mg to about 10 mg of colloidal silicon dioxide.

In one non-limiting aspect of the present disclosure the compositions comprise:

a) from about 0.2 mg to about 25 mg of one or more GLP-1 agonists chosen from dulaglutide, exenatide, liraglutide, lixisenatide, semaglutide, tirzepatide, or mixtures thereof;
b) from about 0.4 mg to about 50 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 5 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 460 mg of sodium bicarbonate; and
e) from about 3 mg to about 480 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 25 mg of semaglutide;
b) from about 0.4 mg to about 50 mg of olive oil;
c) from about 0.05 mg to about 5 mg of deoxycholic acid;
d) from about 1 mg to about 460 mg of sodium bicarbonate; and
e) from about 3 mg to about 480 mg of mannitol, colloidal silicon dioxide, or mixtures thereof.

In one iteration of this aspect of the present disclosure the compositions comprise:
a) from about 0.2 mg to about 25 mg of liraglutide;
b) from about 0.4 mg to about 50 mg of olive oil;
c) from about 0.05 mg to about 5 mg of deoxycholic acid;
d) from about 1 mg to about 460 mg of sodium bicarbonate; and
e) from about 3 mg to about 480 mg of mannitol, colloidal silicon dioxide, or mixtures thereof.

In a further non-limiting aspect of the present disclosure the compositions comprise:
a) from about 0.2 mg to about 20 mg of one or more GLP-1 agonists chosen from dulaglutide, exenatide, liraglutide, lixisenatide, semaglutide, tirzepatide, or mixtures thereof;
b) from about 0.4 mg to about 40 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 4 mg of a bile salt extract wherein the bile salts are an extract containing from about 45% to about 55% by weight of cholic acid, deoxycholic acid, taurocholate, glycocholic acid, and mixtures thereof; from about 1 mg to about 350 mg of sodium bicarbonate; and d)
e) from about 3 mg to about 360 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 20 mg of semaglutide;
b) from about 0.4 mg to about 40 mg of olive oil;
c) from about 0.05 mg to about 4 mg of deoxycholic acid;

d) from about 1 mg to about 350 mg of sodium bicarbonate; and
e) from about 3 mg to about 360 mg of one or more carriers chosen from mannitol, colloidal silicon dioxide, or mixtures thereof.

In another iteration of this aspect of the present disclosure the compositions comprise:
a) from about 0.2 mg to about 20 mg of liraglutide;
b) from about 0.4 mg to about 40 mg of olive oil;
c) from about 0.05 mg to about 4 mg of deoxycholic acid;
d) from about 1 mg to about 350 mg of sodium bicarbonate; and
e) from about 3 mg to about 360 mg of one or more carriers chosen from mannitol, colloidal silicon dioxide, or mixtures thereof.

In further non-limiting aspect of the present disclosure the compositions comprise:
a) from about 0.2 mg to about 20 mg of one or more GLP-1 agonists chosen from dulaglutide, exenatide, liraglutide, lixisenatide, semaglutide, tirzepatide, or mixtures thereof;
b) from about 0.4 mg to about 40 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 4 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 350 mg of sodium bicarbonate; and
e) from about 3 mg to about 360 mg of mannitol, colloidal silicon dioxide, or mixtures thereof.

In another non-limiting aspect of the present disclosure the compositions comprise:
a) from about 0.2 mg to about 12 mg of one or more GLP-1 agonists chosen from dulaglutide, exenatide, liraglutide, lixisenatide, semaglutide, tirzepatide, or mixtures thereof;
b) from about 0.4 mg to about 24 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 3 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 230 mg of sodium bicarbonate; and
e) from about 3 mg to about 240 mg of one or more carriers chosen from sodium N-[8-(2-hydroxybenzoyl) amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 12 mg of semaglutide;
b) from about 0.4 mg to about 24 mg of olive oil;
c) from about 0.05 mg to about 3 mg of deoxycholic acid;
d) from about 1 mg to about 230 mg of sodium bicarbonate; and
e) from about 3 mg to about 240 mg of of mannitol, colloidal silicon dioxide, or mixtures thereof.

In one iteration of this aspect of the present disclosure the compositions comprise:
a) from about 0.2 mg to about 12 mg of liraglutide;
b) from about 0.4 mg to about 24 mg of olive oil;
c) from about 0.05 mg to about 3 mg of deoxycholic acid;
d) from about 1 mg to about 230 mg of sodium bicarbonate; and
e) from about 3 mg to about 240 mg of mannitol, colloidal silicon dioxide, or mixtures thereof.

In a still further non-limiting aspect of the present disclosure the compositions comprise:
a) from about 0.2 mg to about 6 mg of one or more GLP-1 agonists chosen from dulaglutide, exenatide, liraglutide, lixisenatide, semaglutide, tirzepatide, or mixtures thereof;
b) from about 0.4 mg to about 12 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 1.5 mg of a bile salt extract wherein the bile salts are an extract containing from about 45% to about 55% by weight of cholic acid, deoxycholic acid, taurocholate, glycocholic acid, and mixtures thereof; from about 1 mg to about 120 mg of sodium bicarbonate; and d)
e) from about 3 mg to about 125 mg of one or more carriers chosen from sodium N-[8-(2-hydroxybenzoyl) amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 6 mg of semaglutide;
b) from about 0.4 mg to about 12 mg of olive oil;
c) from about 0.05 mg to about 1.5 mg of deoxycholic acid;
d) from about 1 mg to about 120 mg of sodium bicarbonate; and
e) from about 3 mg to about 125 mg of mannitol, colloidal silicon dioxide, or mixtures thereof.

In another iteration of this aspect of the present disclosure the compositions comprise:
a) from about 0.2 mg to about 6 mg of liraglutide;
b) from about 0.4 mg to about 12 mg of olive oil;
c) from about 0.05 mg to about 1.5 mg of deoxycholic acid;
d) from about 1 mg to about 120 mg of sodium bicarbonate; and
e) from about 3 mg to about 125 mg of mannitol, colloidal silicon dioxide, or mixtures thereof.

In a yet another non-limiting aspect of the present disclosure the compositions comprise:
a) from about 0.2 mg to about 4 mg of one or more GLP-1 agonists chosen from dulaglutide, exenatide, liraglutide, lixisenatide, semaglutide, tirzepatide, or mixtures thereof;
b) from about 0.4 mg to about 8 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.75 mg of a bile salt extract wherein the bile salts are an extract containing from about 45% to about 55% by weight of cholic acid, deoxycholic acid, taurocholate, glycocholic acid, and mixtures thereof;

d) from about 1 mg to about 70 mg of sodium bicarbonate; and
e) from about 3 mg to about 75 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 4 mg of semaglutide;
b) from about 0.4 mg to about 8 mg of olive oil;
c) from about 0.05 mg to about 0.75 mg of deoxycholic acid;
d) from about 1 mg to about 70 mg of sodium bicarbonate; and
e) from about 3 mg to about 75 mg of mannitol, colloidal silicon dioxide, or mixtures thereof.

In another iteration of this aspect of the present disclosure the compositions comprise:
a) from about 0.2 mg to about 4 mg of liraglutide;
b) from about 0.4 mg to about 8 mg of olive oil;
c) from about 0.05 mg to about 0.75 mg of deoxycholic acid;
d) from about 1 mg to about 70 mg of sodium bicarbonate; and
e) from about 3 mg to about 75 mg of mannitol, colloidal silicon dioxide, or mixtures thereof.

In a yet still further non-limiting aspect of the present disclosure the compositions comprise:
a) from about 0.2 mg to about 2.5 mg of one or more GLP-1 agonists chosen from dulaglutide, exenatide, liraglutide, lixisenatide, semaglutide, tirzepatide, or mixtures thereof;
b) from about 0.4 mg to about 5 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.5 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 50 mg of sodium bicarbonate; and
e) from about 3 mg to about 50 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 2.5 mg of semaglutide;
b) from about 0.4 mg to about 5 mg of olive oil;
c) from about 0.05 mg to about 0.5 mg of deoxycholic acid;
d) from about 1 mg to about 50 mg of sodium bicarbonate; and
e) from about 3 mg to about 50 mg of mannitol, colloidal silicon dioxide, or mixtures thereof.

In one iteration of this aspect of the present disclosure the compositions comprise:
a) from about 0.2 mg to about 2.5 mg of liraglutide;
b) from about 0.4 mg to about 5 mg of olive oil;
c) from about 0.05 mg to about 0.5 mg of deoxycholic acid;
d) from about 1 mg to about 50 mg of sodium bicarbonate; and
e) from about 3 mg to about 50 mg of mannitol, colloidal silicon dioxide, or mixtures thereof.

In a yet still further non-limiting aspect of the present disclosure the compositions comprise:
a) from about 0.2 mg to about 2 mg of one or more GLP-1 agonists chosen from dulaglutide, exenatide, liraglutide, lixisenatide, semaglutide, tirzepatide, or mixtures thereof;
b) from about 0.4 mg to about 4 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.4 mg of a bile salt extract wherein the bile salts are an extract containing from about 45% to about 55% by weight of cholic acid, deoxycholic acid, taurocholate, glycocholic acid, and mixtures thereof; from about 1 mg to about 40 mg of sodium bicarbonate; and d)
e) from about 3 mg to about 40 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 2 mg of semaglutide;
b) from about 0.4 mg to about 4 mg of olive oil;
c) from about 0.05 mg to about 0.4 mg of deoxycholic acid;
d) from about 1 mg to about 40 mg of sodium bicarbonate; and
e) from about 3 mg to about 40 mg of mannitol, colloidal silicon dioxide, or mixtures thereof.

In one iteration of this aspect of the present disclosure the compositions comprise:
a) from about 0.2 mg to about 2 mg of liraglutide;
b) from about 0.4 mg to about 4 mg of olive oil;
c) from about 0.05 mg to about 0.4 mg of deoxycholic acid;
d) from about 1 mg to about 40 mg of sodium bicarbonate; and
e) from about 3 mg to about 40 mg of mannitol, colloidal silicon dioxide, or mixtures thereof.

In a yet another non-limiting aspect of the present disclosure the compositions comprise:
a) from about 0.2 mg to about 1.5 mg of one or more GLP-1 agonists chosen from dulaglutide, exenatide, liraglutide, lixisenatide, semaglutide, tirzepatide, or mixtures thereof;
b) from about 0.4 mg to about 3 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.3 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 25 mg of sodium bicarbonate; and
e) from about 3 mg to about 25 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 1.5 mg of semaglutide;
b) from about 0.4 mg to about 3 mg of olive oil;
c) from about 0.05 mg to about 0.3 mg of deoxycholic acid;
d) from about 1 mg to about 25 mg of sodium bicarbonate; and
e) from about 3 mg to about 25 mg of mannitol, colloidal silicon dioxide, or mixtures thereof.

In another iteration of this aspect of the present disclosure the compositions comprise:
a) from about 0.2 mg to about 1.5 mg of liraglutide;
b) from about 0.4 mg to about 3 mg of olive oil;
c) from about 0.05 mg to about 0.3 mg of deoxycholic acid;
d) from about 1 mg to about 25 mg of sodium bicarbonate; and
e) from about 3 mg to about 25 mg of mannitol, colloidal silicon dioxide, or mixtures thereof.

In a still yet another non-limiting aspect of the present disclosure the compositions comprise:
a) from about 0.2 mg to about 0.75 mg of one or more GLP-1 agonists chosen from dulaglutide, exenatide, liraglutide, lixisenatide, semaglutide, tirzepatide, or mixtures thereof;
b) from about 0.4 mg to about 1.5 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.15 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 15 mg of sodium bicarbonate; and
e) from about 3 mg to about 15 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 0.75 mg of semaglutide;
b) from about 0.4 mg to about 1.5 mg of olive oil;
c) from about 0.05 mg to about 0.15 mg of deoxycholic acid;
d) from about 1 mg to about 15 mg of sodium bicarbonate; and
e) from about 3 mg to about 15 mg of mannitol, colloidal silicon dioxide, or mixtures thereof.

In another iteration of this aspect of the present disclosure the compositions comprise:
a) from about 0.2 mg to about 0.75 mg of liraglutide;
b) from about 0.4 mg to about 1.5 mg of olive oil;
c) from about 0.05 mg to about 0.15 mg of deoxycholic acid;
d) from about 1 mg to about 15 mg of sodium bicarbonate; and
e) from about 3 mg to about 15 mg of mannitol, colloidal silicon dioxide, or mixtures thereof.

The disclosed compositions comprise from about 0.01 mg to about 50 mg of one or more GLP-1 agonists. In one embodiment the compositions comprise from 0.1 mg to about 30 mg of one or more GLP-1 agonists. In another embodiment the compositions comprise from about 0.1 mg to 10 mg of semaglutide. In a further embodiment the compositions comprise from about 0.01 mg to 5 mg of one or more GLP-1 agonists. In a still further embodiment the compositions comprise from about 0.01 mg to 2 mg of one or more GLP-1 agonists. In a yet further embodiment the compositions comprise from about 0.1 mg to 10 mg of one or more GLP-1 agonists.

The disclosed compositions comprise from about 0.01 mg to about 50 mg of one or more GLP-1 agonists, for example, from about 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg or any fractional amount thereof, for example 6.65 mg, 8.26 mg, of 11.33 mg.

The disclosed compositions comprise from about 0.01 mg to about 100 mg of one or more edible oils. Non-limiting examples of edible oils include olive oil, sunflower oil, coconut oil, canola oil, palm oil, soybean oil, corn oil, safflower oil, peanut oil, or mixtures thereof. In one embodiment the compositions comprise from 0.01 mg to about 50 mg of one or more edible oils. In another embodiment the compositions comprise from about 0.01 mg to 10 mg of edible oils. In a further embodiment the compositions comprise from about 0.01 mg to 2 mg of one or more edible oils. In a still further embodiment the compositions comprise from about 0.05 mg to 4 mg of one or more edible oils. In a yet further embodiment the compositions comprise from about 0.05 mg to 1 mg of one or more edible oils.

The disclosed compositions comprise, for example, from about 0.001 mg to about 100 mg of one or more edible oils, for example, 0.001 mg, 0.002 mg, 0.003 mg, 0.004 mg, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, or 100 mg, or any fractional amount thereof, for example, 10.2 mg, 31.35 mg, or 40.42 mg.

The ratio of the one or more GLP-1 agonists to the one or more edible oils is from about 1:1 to about 1:10, for example, 1:1, 1:2, 1:3, 1:4, 1:5, 1:6, 1:7, 1:8, 1:9, or 1:10, or any fractional amount thereof, for example, 1:1.5, 1:4.2, or 1:8.6. In one embodiment the ratio of the one or more GLP-1 agonist to the one or more edible oils is 1:1. In another embodiment the ratio of the one or more GLP-1 agonist to the one or more edible oils is 1:2. In a further embodiment the ratio of the one or more GLP-1 agonist to the one or more edible oils is 1:3.

The following Tables provide non-limiting examples of compositions which can deliver the required amount of semaglutide of a person in need of treatment.

TABLE C

| Ingredients (mg) | 11 | 12 | 13 | 14 | 15 |
|---|---|---|---|---|---|
| semaglutide | 0.22 | 0.55 | 1.10 | 1.65 | 2.20 |
| olive oil | 0.44 | 1.10 | 2.20 | 3.30 | 4.40 |
| Aeroperl ™ 300 | 2.54 | 6.35 | 12.69 | 19.04 | 25.38 |
| Parteck ™ M 100 | 2.22 | 5.55 | 11.10 | 16.65 | 22.20 |
| Deoxycholic acid | 0.04 | 0.11 | 0.22 | 0.33 | 0.44 |
| Sodium bicarbonate | 4.54 | 11.35 | 22.69 | 34.04 | 45.38 |
| total | 10.00 | 25.00 | 50.00 | 75.00 | 100.00 |

TABLE D

| Ingredients (mg) | 16 | 17 | 18 | 19 | 20 |
|---|---|---|---|---|---|
| semaglutide | 3.30 | 5.51 | 10.99 | 16.48 | 21.98 |
| olive oil | 6.59 | 11.02 | 21.98 | 32.97 | 43.96 |
| Aeroperl ™ 300 | 38.08 | 63.60 | 126.92 | 190.38 | 253.85 |
| Parteck ™ M 100 | 33.30 | 55.59 | 110.99 | 166.48 | 221.98 |
| Deoxycholic acid | 0.66 | 1.10 | 2.20 | 3.30 | 4.40 |
| Sodium bicarbonate | 68.08 | 113.18 | 226.92 | 340.38 | 453.85 |
| total | 150.00 | 250.00 | 500.00 | 750.00 | 1000.00 |

The following Tables provide non-limiting examples of compositions which can deliver the required amount of liraglutide of a person in need of treatment.

TABLE E

| Ingredients (mg) | 21 | 22 | 23 | 24 | 25 |
|---|---|---|---|---|---|
| liraglutide | 0.22 | 0.55 | 1.10 | 1.65 | 2.20 |
| olive oil | 0.44 | 1.10 | 2.20 | 3.30 | 4.40 |
| Aeroperl ™ 300 | 2.54 | 6.35 | 12.69 | 19.04 | 25.38 |
| Parteck ™ M 100 | 2.22 | 5.55 | 11.10 | 16.65 | 22.20 |
| Deoxycholic acid | 0.04 | 0.11 | 0.22 | 0.33 | 0.44 |
| Sodium bicarbonate | 4.54 | 11.35 | 22.69 | 34.04 | 45.38 |
| total | 10.00 | 25.00 | 50.00 | 75.00 | 100.00 |

TABLE F

| Ingredients (mg) | 26 | 27 | 28 | 29 | 30 |
|---|---|---|---|---|---|
| liraglutide | 3.30 | 5.51 | 10.99 | 16.48 | 21.98 |
| olive oil | 6.59 | 11.02 | 21.98 | 32.97 | 43.96 |
| Aeroperl ™ 300 | 38.08 | 63.60 | 126.92 | 190.38 | 253.85 |
| Parteck ™ M 100 | 33.30 | 55.59 | 110.99 | 166.48 | 221.98 |
| Deoxycholic acid | 0.66 | 1.10 | 2.20 | 3.30 | 4.40 |
| Sodium bicarbonate | 68.08 | 113.18 | 226.92 | 340.38 | 453.85 |
| total | 150.00 | 250.00 | 500.00 | 750.00 | 1000.00 |

Bile Salts

The disclosed compositions comprise one or more bile salts as described herein. The source of the bile salts can be any commercially available salts.

For the purposes of the present disclosure the terms "bile salts" and "bile acids" are used interchangeably herein. Bile acids are steroid acids found predominantly in the bile of mammals, for example, oxen, goats, and other cattle. The bile salts are conjugated with the amino acids taurine or glycine to produce bile salts. Extracted bile salts can comprise unconjugated bile acids.

One non-limiting embodiment of bile salts relates to ox bile salt. One example of ox bile salt contains cholic acid (45%-55%) and the balance deoxycholic acid taurocholate and glycocholic acid all of which can be partially or fully conjugated to taurine and glycine. In some embodiments pure acids or acid conjugates are added, for example, deoxycholic acid.

The compositions of the present disclosure comprise from about 1.5% to about 65% by weight of bile salts. In one embodiment the compositions comprise from about 5% to about 55% by weight of bile salts. In one embodiment the compositions comprise from about 10% to about 25% by weight of bile salts. In one embodiment the compositions comprise from about 10% to about 20% by weight of bile salts. In one embodiment the compositions comprise from about 5% to about 15% by weight of bile salts.

The compositions of the present disclosure can comprise from about 0.01% to about 65% by weight of one or more bile salts, for example, 0.01%, 0.02%, 0.03%, 0.04%, 0.05%, 0.06%, 0.07%, 0.08%. 0.09%, 0.1%, 0.2%, 0.3%, 0.4%, 0.5%, 0.6%, 0.7%, 0.8%. 0.9%, 1%, 1.1%, 1.2%, 1.3%, 1.4%, 1.5%, 1.6%, 1.7%, 1.8%, 1.9% or 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% or any fractional amount thereof, for example, 39.7%, 40.23%, or 50.5%.

Cholic acid, also known as $3\alpha$, $7\alpha$, $12\alpha$-trihydroxy-$5\beta$-cholan-24-oic acid is a primary bile acid found in bile extracts. It is insoluble in water (soluble in alcohol and acetic acid), obtained as a white crystalline substance. Salts of cholic acid are referred to as cholates. Cholic acid, along with chenodeoxycholic acid, is one of the two major bile acids produced by the liver of mammals, where it is synthesized from cholesterol. These two major bile acids are roughly equal in concentration in extracts. [4] Bile salts, per se, are made from choloyl-CoA, which exchanges its CoA with either glycine, or taurine, yielding glycocholic and taurocholic acid, respectively. Other bile salts include taurochenodeoxycholic acid and glycochenodeoxycholic acid (derivatives of chenodeoxycholic acid). These together with glycocholic and taurocholic acid make up the major constituents of bile salts.

Disclosed are examples of compositions comprising deoxycholic acid ((4R)-4-[(1R,3aS,3bR,5aR,7R,9aS,9bS,11S,11aR)-7,11-Dihydroxy-9a,11a-dimethylhexadecahydro-1H-cyclopenta[a]phenanthren-1-yl]pentanoic acid). The disclosed compositions can comprise from about 0.01% to about 65% by weight of deoxycholic acid whether as part of a bile salt extract or as the deoxycholic acid alone. In one embodiment the compositions comprise from about 0.01% to about 2% by weight deoxycholic acid, for example, 0.01%, 0.02%, 0.03%, 0.04%, 0.05%, 0.06%, 0.07%, 0.08%. 0.09%, 0.1%, 0.2%, 0.3%, 0.4%, 0.5%, 0.6%, 0.7%, 0.8%. 0.9%, 1%, 1.1%, 1.2%, 1.3%, 1.4%, 1.5%, 1.6%, 1.7%, 1.8%, 1.9% or 2%.

The compositions of the present disclosure comprise from about 0.005 mg to about 250 mg of a bile salt or bile salt extract. In one embodiment the compositions comprise from about 0.01 mg to about 10 mg by weight of one or more bile salts. In one embodiment the compositions comprise from about 0.005 mg to about 0.5 mg of a bile salt or bile salt. In one embodiment the compositions comprise from about 0.01 mg to about 0.5 mg by weight of one or more bile salts. In one embodiment the compositions comprise from about 0.01 mg to about 1 mg by weight of one or more bile salts. In one embodiment the compositions comprise from about 0.005 mg to about 0.1 mg by weight of one or more bile salts or bile salt extracts.

The compositions of the present disclosure comprise from about 0.005 mg to about 250 mg of a bile salt or bile salt extract, for example, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg, 51 mg, 52, mg, 53, mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72, mg, 73, mg, 74 mg, 75 mg, 76 mg, 77 mg, 78 mg, 79 mg, 80 mg, 81 mg, 82, mg, 83, mg, 84 mg, 85 mg, 86 mg, 87 mg, 88 mg, 89 mg, 90 mg, 91 mg, 92, mg, 93, mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg, or any fractional amount thereof, for example 141.8 mg, 172.56 mg, or 202.11 mg.

In non-limiting examples of disclosed compositions, the compositions comprise from about 0.01 mg to 2 mg of deoxycholic acid, for example, 0.005 mg, 0.006 mg, 0.007 mg, 0.008 mg, 0.009 mg, 0.01 mg, 0.02 mg, 0.03 mg, 0.04 mg, 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, or 10 mg of deoxycholic acid.

Sodium Bicarbonate ($NaHCO_3$)

The compositions of the present disclosure comprise from about 35% to about 65% by weight of sodium bicarbonate. In one embodiment the compositions comprise from about 35% to about 55% by weight of sodium bicarbonate. In one embodiment the compositions comprise from about 40% to about 65% by weight of sodium bicarbonate. In one embodiment the compositions comprise from about 40% to about 55% by weight of sodium bicarbonate. In one embodiment the compositions comprise from about 45% to about 60% by weight of sodium bicarbonate.

The compositions of the present disclosure can comprise from about 35% to about 65% by weight of sodium bicarbonate, for example, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% or any fractional amount thereof, for example, 39.7%, 40.23%, or 50.5%.

The compositions of the present disclosure comprise from about 0.5 mg to about 250 mg of sodium bicarbonate. In one embodiment the compositions comprise from about 0.5 mg to about 10 mg of sodium bicarbonate. In one embodiment the compositions comprise from about 1 mg to about 10 mg of sodium bicarbonate.

The compositions of the present disclosure comprise from about 0.5 mg to about 250 mg of sodium bicarbonate, for example, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, or 50 mg, 51 mg, 52, mg, 53, mg, 54 mg, 55 mg, 56 mg, 57 mg, 58 mg, 59 mg, 60 mg, 61 mg, 62, mg, 63, mg, 64 mg, 65 mg, 66 mg, 67 mg, 68 mg, 69 mg, 70 mg, 71 mg, 72, mg, 73, mg, 74 mg, 75 mg, 76 mg, 77 mg, 78 mg, 79 mg, 80 mg, 81 mg, 82, mg, 83, mg, 84 mg, 85 mg, 86 mg, 87 mg, 88 mg, 89 mg, 90 mg, 91 mg, 92, mg, 93, mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg, or any fractional amount thereof, for example 141.8 mg, 172.56 mg, or 202.11 mg.

Carriers

The disclosed compositions comprise from about 15% to about 85% by weight of one or more carriers. In one embodiment the compositions comprise from about 15% to about 50% by weight of one or more carriers. In another embodiment the compositions comprise from about 25% to about 50% by weight of one or more carriers. In a further embodiment the compositions comprise from about 40% to about 55% by weight of one or more carriers. In a still further embodiment the compositions comprise from about 35% to about 65% by weight of one or more carriers. In a yet further embodiment the compositions comprise from about 30% to about 50% by weight of one or more carriers.

The disclosed compositions can comprise, for example, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, by weight of one or more carriers, or any fractional amount thereof, for example 2.5%, 7.66%, or 40.29%.

The disclosed compositions can comprise from about 0.5 mg to about 400 mg of one or more carriers. In one embodiment, the compositions comprise from 1 mg to about 10 mg by weigh of one or more carriers. In another embodiment, the compositions comprise from 2 mg to about 80 mg of one or more carriers. In a further embodiment, the compositions comprise from 1 mg to about 5 mg of one or more carriers. In a still further embodiment, the compositions comprise from 1.5 mg to about 5 mg of one or more carriers.

The disclosed compositions can comprise from about 0.5 mg to about 400 mg of one or more carriers, for example, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 391 mg, 392 mg, 393 mg, 394 mg, 395 mg, 396 mg, 397 mg, 398 mg, 399 mg, or 400 mg or any fractional amount thereof, for example 78.65 mg, 200.7 mg, or 286.75 mg.

In one aspect the disclosed carriers are polysaccharides. Non-limiting examples of poly saccharide carriers include inulin, galactogen, cellulose, chitin, pectin, *psyllium*, guar, hemicellulose, potato starch, and partially hydrolyzed polysaccharides. In another aspect the carriers are sugar alcohols, for example, sorbitol, erythritol, xylitol, lactitol, maltitol, mannitol, hydrogenated starch hydrolysates, isomaltose, or any combination thereof. In a further aspect carrier component is based on a native or chemically modified agar, alginates, carrageenan gum, cellulose, chitosan, chitin, cyclodextrin, dextran, gellan gum, glycogen, glycosaminoglycan, gum karaya, inulin, pectin, polydextrose, xanthan gum, or any other starches, gums or other polysaccharide, including functionalized derivatives, dextrinized, hydrolyzed, oxidized, alkylated, hydroxyalkylated, acetylated, fractionated, and physically modified starches and mixtures thereof. In some embodiments glycerin and/or propylene glycol can be added as a carrier.

In another aspect the carrier is chosen from gum Arabic, tapioca starch, tapioca flour, silicon dioxide, mannitol, colloidal silicon dioxide, and mixture thereof. In a further example the carrier is gum Arabic. In another example the carrier is inulin. In a yet another example the carrier is microcrystalline cellulose. In a still further example, the carrier is D-lactose monohydrate. In a still another example the carrier is quillaia. The carrier can be a combination of gum Arabic, inulin, microcrystalline cellulose, D-lactose monohydrate, or quillaia.

In one embodiment the carrier is chosen from sodium N-[8-(2-hydroxybenzoyl)-amino]caprylate (SNAC), gum Arabic, inulin, mannitol, silicon dioxide, colloidal silicon dioxide, microcrystalline cellulose, D-lactose monohydrate, tapioca starch, tapioca flour, quillaia, or mixtures thereof.

In one embodiment the carrier is chosen from mannitol, colloidal silicon dioxide, or mixtures thereof.

In one non-limiting example the carrier is mannitol, a non-limiting example is Partek™ mannitol, available from Partek Inc. In a further non-limiting example, the carrier is microcrystalline cellulose. In a still further example, the carrier is colloidal silicon dioxide. In a still further example, the carrier is colloidal silicon dioxide. One non-limiting example is Aeroperl® 300 available from IMCD.

Methods

Disclosed herein are methods for treating diabetes, regulating and reducing body weight and improving triglyceride and cholesterol levels. Without wishing to be limited by theory, diabetes can be characterized as a chronic disease that occurs either when the pancreas does not produce enough insulin or when the body cannot effectively use the insulin it produces. For normal, healthy individuals the body breaks down most of the food you eat into sugar (glucose) and releases it into your bloodstream. When your blood sugar goes up, it signals your pancreas to release insulin. Insulin acts like a key to let the blood sugar into your body's cells for use as energy.

With diabetes, the body does not make enough insulin or cannot use it as well as it should. When there isn't enough insulin or the cells stop responding to insulin, too much blood sugar stays in the bloodstream. Over time, that can cause serious health problems, such as heart disease, vision loss, and kidney disease. Therefore, the measure of glucose levels can be a key to monitoring the extent of diabetes in an individual.

Semaglutide, a glucagon-like peptide-1 receptor agonist, has been shown to reduce the risk of adverse cardiovascular events in patients with diabetes. Whether semaglutide can reduce cardiovascular risk associated with overweight and obesity in the absence of diabetes is not unequivocally known.

In a study of 3,297 patients with established cardiovascular disease already on standard treatment, the addition of semaglutide reduced the composite outcome of death from cardiovascular causes, nonfatal myocardial infarction, or nonfatal stroke by 2.3 percentage points as compared with placebo (6.6% vs. 8.9%; number needed to treat=44 over 2.1 years) (See, Marso S P et al.; "SUSTAIN-6 Investigators. Semaglutide and cardiovascular outcomes in patients with type 2 diabetes," N Engl J Med. 2016; 375 (19): 1834-184).

The disclosed methods provide for oral administration of one or more GLP-1 agonists to a subject in need of treatment. The orally available composition can be in any form desired by the formulator. Non-limiting examples of suitable composition forms include tablets, pills, caplets, capsules, and the like.

The disclosed compositions can be administered to a subject to provide any desired amount of one of more GLP-1 agonists. A non-limiting example of GLP-1 dosages includes 3 mg, 7 mg or 14 mg of semaglutide. A further non-limiting example of GLP-1 dosages includes 3 mg, 7 mg or 14 mg of liraglutide.

The following are non-limiting examples of compositions that can deliver 3 mg of semaglutide to a subject in need.

TABLE G

| Ingredients (mg) | 31 | 32 | 33 | 34 | 35 |
|---|---|---|---|---|---|
| semaglutide | 3 | 3 | 3 | 3 | 3 |
| olive oil | 6 | 6 | 6 | 7.5 | 9 |
| Aeroperl ™ 300 | 32 | 35 | 34.6 | 30 | 30 |
| Parteck ™ M 100 | 32 | 30 | 30.3 | 32.5 | 31 |
| Deoxycholic acid | 0.6 | 0.6 | 0.6 | 0.6 | 0.6 |
| Sodium bicarbonate | 61.4 | 60.4 | 61.9 | 61.4 | 61.4 |
| total | 135 | 135 | 136.4 | 135 | 135 |

The following are non-limiting examples of compositions that can deliver 7 mg of semaglutide to a subject in need.

TABLE H

| Ingredients (mg) | 36 | 37 | 38 | 39 | 40 |
|---|---|---|---|---|---|
| semaglutide | 7 | 7 | 7 | 7 | 7 |
| olive oil | 14 | 14 | 14 | 21 | 14 |
| Aeroperl ™ 300 | 79.6 | 79 | 78.6 | 73.5 | 80.6 |
| Parteck ™ M 100 | 70 | 71 | 71.5 | 70 | 70.5 |
| Deoxycholic acid | 1.5 | 1.5 | 1.5 | 1.5 | 1.5 |
| Sodium bicarbonate | 77.9 | 77.5 | 77.4 | 77 | 77.9 |
| total | 250 | 250 | 250 | 250 | 251.5 |

The following are non-limiting examples of compositions that can deliver 14 mg of semaglutide to a subject in need.

TABLE I

| Ingredients (mg) | 41 | 42 | 43 | 44 | 45 |
|---|---|---|---|---|---|
| semaglutide | 14 | 14 | 14 | 14 | 16.48 |
| olive oil | 28 | 28 | 28 | 42 | 32.97 |
| Aeroperl ™ 300 | 160 | 162 | 165 | 158 | 190.38 |
| Parteck ™ M 100 | 140 | 138.4 | 140 | 139.5 | 166.48 |
| Deoxycholic acid | 2.8 | 2.8 | 2.8 | 2.8 | 3.30 |
| Sodium bicarbonate | 285.2 | 284.8 | 280.2 | 273.7 | 340.38 |
| total | 630 | 630 | 630 | 630 | 750.00 |

In one aspect of the disclosed methods, a ramping administration protocol, i.e., where a subject is administered temporally increasing amounts of compositions described herein, can be utilized. For example, a subject could be administered with 100 mg of a composition, as described herein, once per day for 7 days, followed by 200 mg per day for the next 7 days, followed by 300 mg per day for the next 7 days. Administration protocols can also follow a pattern whereby the dosage amount decreases over time. For example, 300 mg of a composition, as described herein, per day for 7 days, followed by 200 mg per day for the next 7 days, followed by 100 mg per day for the next 7 days. In some embodiments, the methods as described herein can be utilized in combination with a calorie restriction protocol in a subject. In certain embodiments, the compositions described herein can be administered before, after, or during a meal. In addition, the appropriate dosage of the compositions can depend, for example, on the condition to be treated, the severity and course of the condition, whether the composition is administered for preventive or therapeutic purposes, previous therapy, the patient's clinical history and response to the composition, the type of composition used, and the discretion of the attending physician. The composition can be suitably administered to the patient at one time or over a series of treatments and can be administered to the patient at any time from diagnosis onwards. The composition can be administered to a subject as the sole composition.

In a further aspect the disclosed compositions can also be administered to a subject in conjunction with other drugs or therapies that were used or are currently used in treating the condition in question for many purposes, such as enhancing efficacy of these drugs or therapies, maintaining efficacy of these drugs or therapies whiling lowering their dosages and thus reducing potentially side effects associated therewith, or gradually allowing the subject to wean from these drugs or therapies to avoid potentially side effects associated therewith. Examples of these drugs or therapies include, but are not limited to dipeptidy peptidase-4 (DPP-4) inhibitors (such as sitagliptin, vildagliptin, saxagliptin, linagliptin, gemigliptin, anagliptin, teneligliptin, alogliptin, trelagliptin, and omarigliptin). The composition and one or more of these drugs or therapies can be delivered simultaneously, at different times, different frequency, and/or by different delivery routes or forms.

The disclosed methods can use any of the herein disclosed compositions. Disclosed herein are methods for treating type-2 diabetes in a subject. Disclosed herein are methods for lowering a subject's A1C. Further disclosed are methods for lowering the body mass of a subject. Also disclosed are methods for regulating the incretin hormone levels of a subject. In one aspect the compositions of the present methods comprise:

a) from about 0.5% to about 20% by weight of one or more GLP-1 agonists;
b) from about 0.5% to about 40% by weight of one or more edible oils;
c) from about 1.5% to about 65% by weight of a bile salt extract;
d) from about 35% to about 65% by weight of sodium bicarbonate; and
e) from about 15% to about 85% by weight of one or more carriers.

In one embodiment of this aspect the compositions of the disclosed methods comprise:
a) from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of one or more edible oils chosen from olive oil, sunflower oil, coconut oil, canola oil, palm oil, soybean oil, corn oil, safflower oil, peanut oil, or mixtures thereof;
c) from about 1.5% to about 65% by weight of a bile salt extract wherein the bile salt extract contains from about 45% to about 55% by weight of a bile salt selected from the group consisting of cholic acid, deoxycholic acid, taurocholate, glycocholic acid, or a mixture thereof;
d) from about 35% to about 65% by weight of sodium bicarbonate; and
e) from about 15% to about 85% by weight of one or more carriers.

In one iteration of this embodiment of this aspect the compositions of the disclosed methods comprise:
a) from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of one or more edible oils chosen from olive oil, sunflower oil, coconut oil, canola oil, palm oil, soybean oil, corn oil, safflower oil, peanut oil, or mixtures thereof;
c) from about 1.5% to about 65% by weight of a bile salt extract wherein the bile salt extract contains from about 45% to about 55% by weight of a bile salt selected from the group consisting of cholic acid, deoxycholic acid, taurocholate, glycocholic acid, or mixtures thereof;
d) from about 35% to about 65% by weight of sodium bicarbonate; and
e) from about 15% to about 85% by weight of one or more carriers chosen from gum Arabic, inulin, mannitol, silicon dioxide, colloidal silicon dioxide, microcrystalline cellulose, D-lactose monohydrate, tapioca starch, tapioca flour, quillaia, or mixtures thereof.

In another iteration of this embodiment of this aspect the compositions of the disclosed methods comprise:
a) from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of olive oil;
c) from about 1.5% to about 65% by weight of a bile salt extract wherein the bile salt extract contains from about 45% to about 55% by weight of a bile salt selected from the group consisting of cholic acid, deoxycholic acid, taurocholate, glycocholic acid, or mixtures thereof;
d) from about 35% to about 65% by weight of sodium bicarbonate; and
e) from about 15% to about 85% by weight of one or more carriers chosen from sodium N-[8-(2-hydroxybenzoyl)amino]caprylate (SNAC), gum Arabic, inulin, mannitol, silicon dioxide, colloidal silicon dioxide, microcrystalline cellulose, D-lactose monohydrate, tapioca starch, tapioca flour, quillaia, or mixtures thereof.

In a further iteration of this embodiment of this aspect the compositions of the disclosed methods comprise:
a from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of olive oil;
c) from about 1.5% to about 65% by weight of deoxycholic acid;
d) from about 35% to about 65% by weight of sodium bicarbonate; and
e) from about 15% to about 85% by weight of one or more carriers chosen from about 15% to about 85% by weight of one or more carriers chosen from sodium N-[8-(2-hydroxybenzoyl)amino]caprylate (SNAC), gum Arabic, inulin, mannitol, silicon dioxide, colloidal silicon dioxide, microcrystalline cellulose, D-lactose monohydrate, tapioca starch, tapioca flour, quillaia, or mixtures thereof.

In another iteration of this embodiment of this aspect the compositions of the disclosed methods comprise:
a) from about 0.5% to about 20% by weight of one or more GLP-1 agonists chosen from dulaglutide, exenatide, liraglutide, lixisenatide, semaglutide, tirzepatide, or mixtures thereof;
b) from about 0.5% to about 40% by weight of olive oil;
c) from about 1.5% to about 65% by weight deoxycholic acid;
d) from about 35% to about 65% by weight of sodium bicarbonate; and
e) from about 15% to about 85% by weight of one or more carriers chosen from gum Arabic, colloidal silicon dioxide, tapioca starch, or mixtures thereof.

In one non-limiting example of this iteration of this embodiment of this aspect the compositions of the disclosed methods comprise:
a) from about 0.5% to about 20% by weight of dulaglutide;
b) from about 0.5% to about 40% by weight of olive oil;
c) from about 1.5% to about 65% by weight deoxycholic acid;
d) from about 35% to about 65% by weight of sodium bicarbonate; and
e) from about 15% to about 85% by weight of gum Arabic.

In a further non-limiting example of this iteration of this embodiment of this aspect the compositions of the disclosed methods comprise:
a) from about 0.5% to about 20% by weight of exenatide;
b) from about 0.5% to about 40% by weight of olive oil;
c) from about 1.5% to about 65% by weight deoxycholic acid;
d) from about 35% to about 65% by weight of sodium bicarbonate; and
e) from about 15% to about 85% by weight of gum Arabic.

In another non-limiting example of this iteration of this embodiment of this aspect the compositions of the disclosed methods comprise:
a) from about 0.5% to about 20% by weight of liraglutide;
b) from about 0.5% to about 40% by weight of olive oil;
c) from about 1.5% to about 65% by weight deoxycholic acid;

d) from about 35% to about 65% by weight of sodium bicarbonate; and
e) from about 15% to about 85% by weight of gum Arabic.

In a yet further non-limiting example of this iteration of this embodiment of this aspect the compositions of the disclosed methods comprise:
a) from about 0.5% to about 20% by weight of lixisenatide;
b) from about 0.5% to about 40% by weight of olive oil;
c) from about 1.5% to about 65% by weight deoxycholic acid;
d) from about 35% to about 65% by weight of sodium bicarbonate; and
e) from about 15% to about 85% by weight of gum Arabic.

In a still yet further non-limiting example of this iteration of this embodiment of this aspect the compositions of the disclosed methods comprise:
a) from about 0.5% to about 20% by weight of semaglutide;
b) from about 0.5% to about 40% by weight of olive oil;
c) from about 1.5% to about 65% by weight deoxycholic acid;
d) from about 35% to about 65% by weight of sodium bicarbonate; and
e) from about 15% to about 85% by weight of gum Arabic.

In another yet further non-limiting example of this iteration of this embodiment of this aspect the compositions of the disclosed methods comprise:
a) from about 0.5% to about 20% by weight of tirzepatide;
b) from about 0.5% to about 40% by weight of olive oil;
c) from about 1.5% to about 65% by weight deoxycholic acid;
d) from about 35% to about 65% by weight of sodium bicarbonate; and
e) from about 15% to about 85% by weight of gum Arabic.

In another aspect of the present disclosure the compositions of the disclosed method comprise:
a) from about 0.5% to about 20% by weight of semaglutide;
b) from about 0.5% to about 40% by weight of sunflower oil;
c) from about 1.5% to about 65% by weight of a bile salt extract;
d) from about 35% to about 65% by weight of sodium bicarbonate; and
e) from about 15% to about 65% by weight of one or more carriers.

In one embodiment of this aspect the compositions of the disclosed method comprise:
a) from about 1% to about 3% by weight of semaglutide;
b) from about 1% to about 25% by weight of sunflower oil;
c) from about 35% to about 65% by weight of a bile salt extract wherein the bile salts are an extract containing from about 45% to about 55% by weight of cholic acid, deoxycholic acid, taurocholate, glycocholic acid, and mixtures thereof;
d) from about 35% to about 65% by weight of sodium bicarbonate; and
e) from about 15% to about 65% by weight of one or more carriers.

In a further embodiment of this aspect the compositions of the disclosed method comprise:
a) from about 1% to about 3% by weight of semaglutide;
b) from about 1% to about 25% by weight of high oleic acid sunflower oil;
c) from about 35% to about 65% by weight of a bile salt extract;
d) from about 35% to about 65% by weight of sodium bicarbonate; and
e) from about 15% to about 65% by weight of one or more carriers chosen from gum Arabic, tapioca starch, tapioca flour, silicon dioxide, mannitol, colloidal silicon dioxide, and mixture thereof.

In another embodiment of this aspect the compositions of the disclosed method comprise:
a) from about 1% to about 3% by weight of semaglutide;
b) from about 1% to about 25% by weight of high oleic acid sunflower oil;
c) from about 35% to about 65% by weight of a bile salt extract wherein the bile salts are an extract containing from about 45% to about 55% by weight of cholic acid, deoxycholic acid, taurocholate, glycocholic acid, and mixtures thereof;
d) from about 35% to about 65% by weight of sodium bicarbonate; and
e) from about 15% to about 65% by weight of one or more carriers chosen from gum Arabic, tapioca starch, tapioca flour, silicon dioxide, mannitol, colloidal silicon dioxide, and mixture thereof.

In another aspect of the present disclosure the compositions of the disclosed method comprise:
a) from about 1% to about 20% by weight of semaglutide;
b) from about 0.5% to about 40% by weight of high oleic acid sunflower oil;
c) from about 1.5% to about 15% by weight of deoxycholic acid;
d) from about 35% to about 65% by weight of sodium bicarbonate; and
e) from about 15% to about 65% by weight of one or more carriers.

In one embodiment of this aspect the compositions of the disclosed method comprise:
a) from about 1% to about 20% by weight of semaglutide;
b) from about 0.5% to about 40% by weight of high oleic acid sunflower oil;
c) from about 1.5% to about 15% by weight of deoxycholic acid;
d) from about 35% to about 65% by weight of sodium bicarbonate; and
e) from about 15% to about 65% by weight of one or more carriers In a further embodiment of this aspect the compositions of the disclosed method comprise:
a) from about 1% to about 20% by weight of semaglutide;
b) from about 0.5% to about 40% by weight of high oleic acid sunflower oil;
c) from about 1.5% to about 15% by weight of deoxycholic acid;
d) from about 35% to about 65% by weight of sodium bicarbonate; and
e) from about 15% to about 65% by weight of one or more carriers chosen from gum Arabic, tapioca starch, tapioca flour, silicon dioxide, mannitol, colloidal silicon dioxide, and mixture thereof.

In a further aspect of the disclosure the compositions of the disclosed methods comprise:

a) from about 0.1 mg to about 50 mg of one or more GLP-1 agonists chosen from dulaglutide, exenatide, liraglutide, lixisenatide, semaglutide, tirzepatide, or mixtures thereof;
b) from about 0.1 mg to about 100 mg of one or more edible oils;
c) from about 5 mg to about 250 mg of a bile salt extract;
d) from about 20 mg to about 250 mg of sodium bicarbonate; and
e) from about 50 mg to about 400 mg of one or more carriers.

In one embodiment of this aspect of the present disclosure the compositions of the disclosed method comprise:
a) from about 0.1 mg to about 50 mg of one or more GLP-1 agonists chosen from dulaglutide, exenatide, liraglutide, lixisenatide, semaglutide, tirzepatide, or mixtures thereof;
b) from about 0.1 mg to about 100 mg of one or more edible oils chosen from olive oil, sunflower oil, coconut oil, canola oil, palm oil, soybean oil, corn oil, safflower oil, peanut oil, or mixtures thereof;
c) from about 100 mg to about 250 mg of a bile salt extract wherein the bile salts are an extract containing from about 45% to about 55% by weight of cholic acid, deoxycholic acid, taurocholate, glycocholic acid, and mixtures thereof;
d) from about 20 mg to about 250 mg of sodium bicarbonate; and
e) from about 50 mg to about 350 mg of one or more carriers.

In one iteration of this embodiment of this aspect of the present disclosure the compositions of the disclosed method comprise:
a) from about 0.1 mg to about 50 mg of one or more GLP-1 agonists chosen from dulaglutide, exenatide, liraglutide, lixisenatide, semaglutide, tirzepatide, or mixtures thereof;
b) from about 0.1 mg to about 100 mg of one or more edible oils chosen from olive oil, sunflower oil, coconut oil, canola oil, palm oil, soybean oil, corn oil, safflower oil, peanut oil, or mixtures thereof;
c) from about 100 mg to about 250 mg of a bile salt extract wherein the bile salts are an extract containing from about 45% to about 55% by weight of cholic acid, deoxycholic acid, taurocholate, glycocholic acid, and mixtures thereof;
d) from about 20 mg to about 250 mg of sodium bicarbonate; and
e) from about 50 mg to about 350 mg of one or more carriers chosen from gum Arabic, inulin, mannitol, silicon dioxide, colloidal silicon dioxide, microcrystalline cellulose, D-lactose monohydrate, tapioca starch, tapioca flour, quillaia, or mixtures thereof.

In another iteration of this embodiment of this aspect of the present disclosure the compositions of the disclosed method comprise:
a) from about 0.1 mg to about 50 mg of one or more GLP-1 agonists chosen from dulaglutide, exenatide, liraglutide, lixisenatide, semaglutide, tirzepatide, or mixtures thereof;
b) from about 0.1 mg to about 100 mg of olive oil;
c) from about 100 mg to about 250 mg of deoxycholic acid;
d) from about 20 mg to about 250 mg of sodium bicarbonate; and
e) from about 50 mg to about 350 mg of one or more carriers sodium N-[8-(2-hydroxybenzoyl)amino]caprylate (SNAC), gum Arabic, inulin, mannitol, silicon dioxide, colloidal silicon dioxide, microcrystalline cellulose, D-lactose monohydrate, tapioca starch, tapioca flour, quillaia, or mixtures thereof.

In a non-limiting example of this iteration of this embodiment of this aspect of the present disclosure the compositions of the disclosed method comprise:
a) from about 1 mg to about 10 mg dulaglutide;
b) from about 1 mg to about 50 mg of olive oil;
c) from about 10 mg to about 40 mg of deoxycholic acid;
d) from about 50 mg to about 100 mg of sodium bicarbonate; and
e) from about 50 mg to about 350 mg of gum Arabic.

In another non-limiting example of this iteration of this embodiment of this aspect of the present disclosure the compositions of the disclosed method comprise:
a) from about 1 mg to about 10 mg exenatide;
b) from about 1 mg to about 50 mg of olive oil;
c) from about 10 mg to about 40 mg of deoxycholic acid;
d) from about 50 mg to about 100 mg of sodium bicarbonate; and
e) from about 50 mg to about 350 mg of gum Arabic.

In a further non-limiting example of this iteration of this embodiment of this aspect of the present disclosure the compositions of the disclosed method comprise:
a) from about 1 mg to about 10 mg liraglutide;
b) from about 1 mg to about 50 mg of olive oil;
c) from about 10 mg to about 40 mg of deoxycholic acid;
d) from about 50 mg to about 100 mg of sodium bicarbonate; and
e) from about 50 mg to about 350 mg of gum Arabic.

In a still further non-limiting example of this iteration of this embodiment of this aspect of the present disclosure the compositions of the disclosed method comprise:
a) from about 1 mg to about 10 mg lixisenatide;
b) from about 1 mg to about 50 mg of olive oil;
c) from about 10 mg to about 40 mg of deoxycholic acid;
d) from about 50 mg to about 100 mg of sodium bicarbonate; and
e) from about 50 mg to about 350 mg of gum Arabic.

In a yet still further non-limiting example of this iteration of this embodiment of this aspect of the present disclosure the compositions of the disclosed method comprise:
a) from about 1 mg to about 10 mg semaglutide;
b) from about 1 mg to about 50 mg of olive oil;
c) from about 10 mg to about 40 mg of deoxycholic acid;
d) from about 50 mg to about 100 mg of sodium bicarbonate; and
e) from about 50 mg to about 350 mg of gum Arabic.

In another still further non-limiting example of this iteration of this embodiment of this aspect of the present disclosure the compositions of the disclosed method comprise:
a) from about 1 mg to about 10 mg tirzepatide;
b) from about 1 mg to about 50 mg of olive oil;
c) from about 10 mg to about 40 mg of deoxycholic acid;
d) from about 50 mg to about 100 mg of sodium bicarbonate; and
e) from about 50 mg to about 350 mg of gum Arabic.

In another iteration of this embodiment of this aspect of the present disclosure the compositions of the disclosed method comprise:
a) from about 5 mg to about 10 mg semaglutide;
b) from about 5 mg to about 30 mg of olive oil;
c) from about 10 mg to about 40 mg of deoxycholic acid;
d) from about 25 mg to about 50 mg of sodium bicarbonate; and
e) from about 50 mg to about 350 mg of gum Arabic.

In a further iteration of this embodiment of this aspect of the present disclosure the compositions of the disclosed method comprise:
a) from about 5 mg to about 10 mg liraglutide;
b) from about 5 mg to about 30 mg of sunflower oil;
c) from about 10 mg to about 40 mg of deoxycholic acid;
d) from about 25 mg to about 50 mg of sodium bicarbonate; and
e) from about 50 mg to about 350 mg of gum Arabic.

In one non-limiting aspect of the present disclosure the compositions which can be administered to a subject in need of treatment comprise:
a) from about 0.2 mg to about 25 mg of one or more GLP-1 agonists chosen from dulaglutide, exenatide, liraglutide, lixisenatide, semaglutide, tirzepatide, or mixtures thereof;
b) from about 0.4 mg to about 50 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 5 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 460 mg of sodium bicarbonate; and
e) from about 3 mg to about 480 mg of one or more carriers chosen from sodium N-[8-(2-hydroxybenzoyl) amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 25 mg of semaglutide;
b) from about 0.4 mg to about 50 mg of olive oil;
c) from about 0.05 mg to about 5 mg of deoxycholic acid;
d) from about 1 mg to about 460 mg of sodium bicarbonate; and
e) from about 3 mg to about 480 mg of mannitol, colloidal silicon dioxide, or mixtures thereof.

In a further non-limiting aspect of the present disclosure the compositions which can be administered to a subject in need of treatment comprise:
a) from about 0.2 mg to about 20 mg of one or more GLP-1 agonists chosen from dulaglutide, exenatide, liraglutide, lixisenatide, semaglutide, tirzepatide, or mixtures thereof;
b) from about 0.4 mg to about 40 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 4 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 350 mg of sodium bicarbonate; and
e) from about 3 mg to about 360 mg of one or more carriers chosen from sodium N-[8-(2-hydroxybenzoyl) amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 20 mg of semaglutide;
b) from about 0.4 mg to about 40 mg of olive oil;
c) from about 0.05 mg to about 4 mg of deoxycholic acid;
d) from about 1 mg to about 350 mg of sodium bicarbonate; and
e) from about 3 mg to about 360 mg of mannitol, colloidal silicon dioxide, or mixtures thereof.

In further non-limiting aspect of the present disclosure the compositions which can be administered to a subject in need of treatment comprise:
a) from about 0.2 mg to about 20 mg of one or more GLP-1 agonists chosen from dulaglutide, exenatide, liraglutide, lixisenatide, semaglutide, tirzepatide, or mixtures thereof;
b) from about 0.4 mg to about 40 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 4 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 350 mg of sodium bicarbonate; and
e) from about 3 mg to about 360 mg of mannitol, colloidal silicon dioxide, or mixtures thereof.

In another non-limiting aspect of the present disclosure the compositions which can be administered to a subject in need of treatment comprise:
a) from about 0.2 mg to about 12 mg of one or more GLP-1 agonists chosen from dulaglutide, exenatide, liraglutide, lixisenatide, semaglutide, tirzepatide, or mixtures thereof;
b) from about 0.4 mg to about 24 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 3 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 230 mg of sodium bicarbonate; and
e) from about 3 mg to about 240 mg of one or more carriers chosen from sodium N-[8-(2-hydroxybenzoyl) amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 12 mg of semaglutide;
b) from about 0.4 mg to about 24 mg of olive oil;
c) from about 0.05 mg to about 3 mg of deoxycholic acid;
d) from about 1 mg to about 230 mg of sodium bicarbonate; and
e) from about 3 mg to about 240 mg of mannitol, colloidal silicon dioxide, microcrystalline cellulose, D-lactose monohydrate, tapioca starch, tapioca flour, quillaia, or mixtures thereof.

In a still further non-limiting aspect of the present disclosure the compositions which can be administered to a subject in need of treatment comprise:

a) from about 0.2 mg to about 6 mg of one or more GLP-1 agonists chosen from dulaglutide, exenatide, liraglutide, lixisenatide, semaglutide, tirzepatide, or mixtures thereof;
b) from about 0.4 mg to about 12 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 1.5 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 120 mg of sodium bicarbonate; and
e) from about 3 mg to about 125 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 6 mg of semaglutide;
b) from about 0.4 mg to about 12 mg of olive oil;
c) from about 0.05 mg to about 1.5 mg of deoxycholic acid;
d) from about 1 mg to about 120 mg of sodium bicarbonate; and
e) from about 3 mg to about 125 mg of mannitol, colloidal silicon dioxide, or mixtures thereof.

In a yet another non-limiting aspect of the present disclosure the compositions which can be administered to a subject in need of treatment comprise:
a) from about 0.2 mg to about 4 mg of one or more GLP-1 agonists chosen from dulaglutide, exenatide, liraglutide, lixisenatide, semaglutide, tirzepatide, or mixtures thereof;
b) from about 0.4 mg to about 8 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.75 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 70 mg of sodium bicarbonate; and
e) from about 3 mg to about 75 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 4 mg of semaglutide;
b) from about 0.4 mg to about 8 mg of olive oil;
c) from about 0.05 mg to about 0.75 mg of deoxycholic acid;
d) from about 1 mg to about 70 mg of sodium bicarbonate; and
e) from about 3 mg to about 75 mg of mannitol, colloidal silicon dioxide, or mixtures thereof.

In a yet still further non-limiting aspect of the present disclosure the compositions which can be administered to a subject in need of treatment comprise:
a) from about 0.2 mg to about 2.5 mg of one or more GLP-1 agonists chosen from dulaglutide, exenatide, liraglutide, lixisenatide, semaglutide, tirzepatide, or mixtures thereof;
b) from about 0.4 mg to about 5 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.5 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 50 mg of sodium bicarbonate; and
e) from about 3 mg to about 50 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 2.5 mg of semaglutide;
b) from about 0.4 mg to about 5 mg of olive oil;
c) from about 0.05 mg to about 0.5 mg of deoxycholic acid;
d) from about 1 mg to about 50 mg of sodium bicarbonate; and
e) from about 3 mg to about 50 mg of mannitol, colloidal silicon dioxide, or mixtures thereof.

In a yet still further non-limiting aspect of the present disclosure the compositions which can be administered to a subject in need of treatment comprise:
a) from about 0.2 mg to about 2 mg of one or more GLP-1 agonists chosen from dulaglutide, exenatide, liraglutide, lixisenatide, semaglutide, tirzepatide, or mixtures thereof;
b) from about 0.4 mg to about 4 mg of one or more edible oils chosen from olive oil, sunflower oil, coconut oil, canola oil, palm oil, soybean oil, corn oil, safflower oil, peanut oil, or mixtures thereof;
c) from about 0.05 mg to about 0.4 mg of a bile salt extract wherein the bile salts are an extract containing from about 45% to about 55% by weight of cholic acid, deoxycholic acid, taurocholate, glycocholic acid, and mixtures thereof;
d) from about 1 mg to about 40 mg of sodium bicarbonate; and
e) from about 3 mg to about 40 mg of one or more carriers chosen from sodium N-[8-(2-hydroxybenzoyl)amino]caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
a) from about 0.2 mg to about 2 mg of semaglutide;
b) from about 0.4 mg to about 4 mg of olive oil;
c) from about 0.05 mg to about 0.4 mg of deoxycholic acid;
d) from about 1 mg to about 40 mg of sodium bicarbonate; and e) from about 3 mg to about 40 mg of mannitol, colloidal silicon dioxide, or mixtures thereof.

In a yet another non-limiting aspect of the present disclosure the compositions which can be administered to a subject in need of treatment comprise:
- a) from about 0.2 mg to about 1.5 mg of one or more GLP-1 agonists chosen from dulaglutide, exenatide, liraglutide, lixisenatide, semaglutide, tirzepatide, or mixtures thereof;
- b) from about 0.4 mg to about 3 mg of one or more edible oils chosen from olive oil, sunflower oil, coconut oil, canola oil, palm oil, soybean oil, corn oil, safflower oil, peanut oil, or mixtures thereof;
- c) from about 0.05 mg to about 0.3 mg of a bile salt extract wherein the bile salts are an extract containing from about 45% to about 55% by weight of cholic acid, deoxycholic acid, taurocholate, glycocholic acid, and mixtures thereof;
- d) from about 1 mg to about 25 mg of sodium bicarbonate; and
- e) from about 3 mg to about 25 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
- a) from about 0.2 mg to about 1.5 mg of semaglutide;
- b) from about 0.4 mg to about 3 mg of olive oil;
- c) from about 0.05 mg to about 0.3 mg of deoxycholic acid;
- d) from about 1 mg to about 25 mg of sodium bicarbonate; and
- e) from about 3 mg to about 25 mg of mannitol, colloidal silicon dioxide, or mixtures thereof.

In a still yet another non-limiting aspect of the present disclosure the compositions which can be administered to a subject in need of treatment comprise:
- a) from about 0.2 mg to about 0.75 mg of one or more GLP-1 agonists chosen from dulaglutide, exenatide, liraglutide, lixisenatide, semaglutide, tirzepatide, or mixtures thereof;
- b) from about 0.4 mg to about 1.5 mg of one or more edible oils chosen from olive oil, sunflower oil, coconut oil, canola oil, palm oil, soybean oil, corn oil, safflower oil, peanut oil, or mixtures thereof;
- c) from about 0.05 mg to about 0.15 mg of a bile salt extract wherein the bile salts are an extract containing from about 45% to about 55% by weight of cholic acid, deoxycholic acid, taurocholate, glycocholic acid, and mixtures thereof;
- d) from about 1 mg to about 15 mg of sodium bicarbonate; and
- e) from about 3 mg to about 15 mg of one or more carriers chosen from sodium N-[8-(2-hydroxybenzoyl)amino] caprylate (SNAC) gum Arabic, inulin, mannitol, silicon dioxide, colloidal silicon dioxide, microcrystalline cellulose, D-lactose monohydrate, tapioca starch, tapioca flour, quillaia, or mixtures thereof.

In one iteration of this aspect of the present disclosure the compositions comprise:
- a) from about 0.2 mg to about 0.75 mg of semaglutide;
- b) from about 0.4 mg to about 1.5 mg of olive oil;
- c) from about 0.05 mg to about 0.15 mg of deoxycholic acid;
- d) from about 1 mg to about 15 mg of sodium bicarbonate; and
- e) from about 3 mg to about 15 mg of mannitol, colloidal silicon dioxide, or mixtures thereof.

General Procedure for Preparing Disclosed Compositions

Study 1

The following is an outline of the procedure for preparing the disclosed compositions:
- a) reduce to a fine powder 29 Rybelsus™ tablets containing 14 mg of semaglutide each;
- b) combine powder from (a) with high oleic acid sunflower oil at 40° C. to form an admixture;
- c) add excipients and mix until homogeneous;
- d) dry the homogeneous mixture from step (c) at 50° C. to form a dehydrated powder;
- e) cool the dehydrated powder;
- f) combine the dehydrated powder with sodium bicarbonate and ox bile extract to form a free-flowing powder final blend;
- g) fill capsules with the final blend.

Process for Preparing Test Composition for Study 1

Grind semaglutide tablets (29) wherein each tablet contained 14 mg of semaglutide in a mortar and pastel after which the resulting powder is screened using a stainless-steel mesh. Heat the high oleic acid sunflower oil to 40° C. and add the crushed semaglutide with efficient mixing. Once the oil dispersion is homogeneous, gum Arabic and Aeroperl 300 are added with low-speed mixing to completely infuse the dispersion with the carriers. Efficient mixing results in a homogeneous powder after about 10 minutes. Transfer and evenly disperse the powder to a stainless-steel tray and place in a pre-heated oven at 50° C. oven for 2 hours. Remove the tray and cool for 10 minutes. The powder is then re-screened. The cooled powder is then combined with the sodium bicarbonate and ox bile extract in a bio safety cabinet for 3 to 5 minutes at low to medium speed. The resulting free flowing product is used to fill size 00 capsules with 465.86 mg of the final product.

The resulting capsules were used for the following Study 1 human clinical trials. Each Capsule contained the amounts in Table 1:

TABLE 1

| Ingredients | mg | % |
|---|---|---|
| Semaglutide | 1.75 | 0.38 |
| Rybelsus ™ excipients[1] | 49.5 | 10.63 |
| Sunflower oil | 51.25 | 11 |
| Bile salt extract[2] | 97 | 20.8 |
| Sodium bicarbonate | 80 | 17.17 |
| Gum Arabic | 93.18 | 20 |
| Aeroperl 300 ™[3] | 93.18 | 20 |
| Total | 465.86 | 100 |

[1]contains magnesium stearate, microcrystalline cellulose, Povidone K90 ™, and sodium salcaproate.
[2]ox bile extract containing from about 45% to about 55% of an admixture of cholic acid, deoxycholic acid, taurocholate, and glycocholic acid.
[3]microcrystalline cellulose.

Human Clinical Study 1

This study was conducted in two parts. In the first part of this study 3 volunteers were administered Rybelsus™ tablets containing 7 mg of semaglutide for the control group while 4 volunteers in the study group were given 4 capsules containing the ingredients listed in Table 1 for an effective does of 7 mg of semaglutide.

The second part of this study involved a crossover leg wherein the subjects receiving Rybelsus™ tablets in the first study were given 4 capsules of the study composition from Table 1 for an effective amount of 7 mg of semaglutide and the subjects receiving the study composition were administered Rybelsus™ tablets containing 7 mg of semaglutide.

Semaglutide Levels

Blood was examined by a third-party laboratory using a validated bioassay 18 times over the first 10 hours of the Study, and once again 24 hours after the dose was administered. Each subject fasted for 12 hours prior to testing. Subjects were supervised and monitored in the Study site over the entire 10-hour duration post dosing, and then allowed to depart, resume normal activities and return to the Study site the following day for performance of the 24-hour evaluation time point.

The first post-baseline blood was sampled 20 minutes after oral administration and, at that point in time, the study group blood semaglutide level was ~125% higher than that of the Control. At each of the 19 blood sample time points, the study group blood semaglutide levels were higher than the Control levels. Furthermore, the study group peak was achieved faster at 120 minutes (as compared to 160 minutes for the Control) and with a 16% higher blood semaglutide level than the Control. The blood semaglutide levels achieved with the Control were proportional to those achieved in similar single dose cross-over Rybelsus™ development informing studies, further suggesting that the blood semaglutide level gains evidenced by the study group formulation were notably distinct relative to the commercial product. A final blood draw was taken 24 hours after the beginning of testing. Subjects were allowed to return to their normal schedule prior to the 24 hour final blood draw.

Table 2 provides the semaglutide blood levels for the subjects in phase 1 of the Study.

TABLE 2

(all values are in nmol/L)

| Time of draw (min,) | Rybelsus ™ | Study composition |
|---|---|---|
| 0 | 0.00 | 0.00 |
| 20 | 0.40 | 0.90 |
| 40 | 1.33 | 2.40 |
| 60 | 3.27 | 4.38 |
| 80 | 5.47 | 6.93 |
| 100 | 6.83 | 8.13 |
| 120 | 7.07 | 8.53 |
| 140 | 7.27 | 8.43 |
| 160 | 7.33 | 8.45 |
| 180 | 7.33 | 8.38 |
| 210 | 7.20 | 8.20 |
| 240[1] | 7.07 | 8.05 |
| 300 | 6.97 | 7.85 |
| 360[2] | 6.87 | 7.63 |

TABLE 2-continued (all values are in nmol/L)

| Time of draw (min,) | Rybelsus ™ | Study composition |
|---|---|---|
| 420 | 6.70 | 7.63 |
| 480 | 6.57 | 7.03 |
| 540 | 6.47 | 7.28 |
| 600 | 6.33 | 7.03 |
| 24 hr | 3.77 | 4.70 |

[1]Participants were offered a meal.
[2]Participants were offered a snack.

Figure 3:
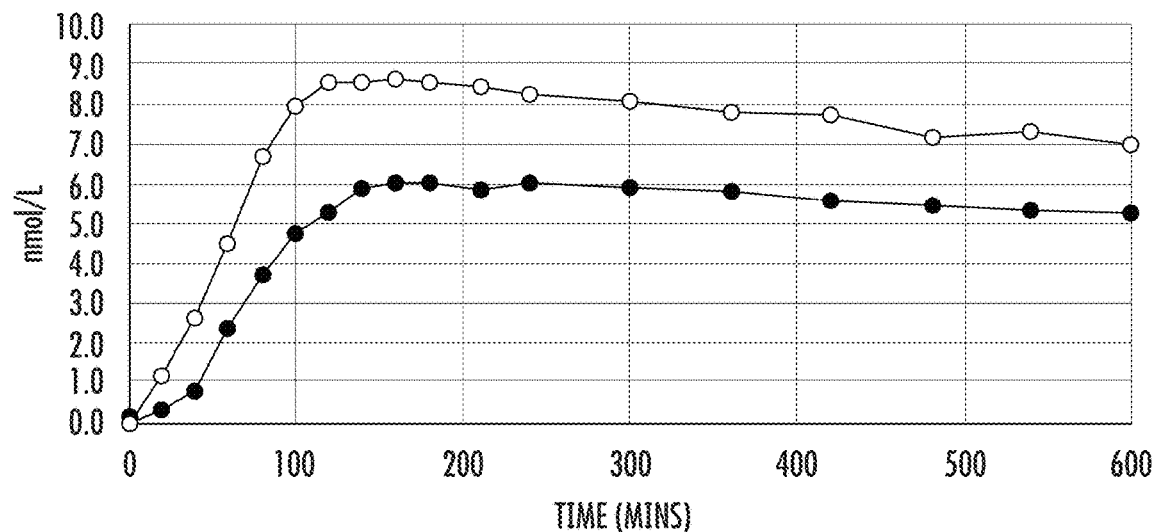
FIG. 3 is a plot of the semaglutide levels in nmol/L of the combined results (first leg and crossover study) for the subjects administered Rybelsus™ 7 mg tablet (●) versus the combined study subjects given the composition of Table 1 times 4 (○) for an effective amount of semaglutide of 7 mg.

Table 3 below shows semaglutide blood concentration of the combined data from phase 1 of the study together with the crossover study group (subjects that received Rybelsus™ now receive the composition from Table 1 and vice versus). The combined data from Tables 2 and 3 are depicted in FIG. 3.

TABLE 3

(all values are in nmol/L)

| Time of draw (min,) | Rybelsus ™ | Study composition |
|---|---|---|
| 0 | 0.2 | 0.0 |
| 20 | 0.3 | 1.2 |
| 40 | 0.8 | 2.6 |
| 60 | 2.3 | 4.5 |
| 80 | 3.7 | 6.7 |
| 100 | 4.8 | 8.0 |
| 120 | 5.3 | 8.6 |
| 140 | 5.9 | 8.6 |
| 160 | 6.1 | 8.6 |
| 180 | 6.0 | 8.6 |
| 210 | 5.8 | 8.4 |
| 240[1] | 6.0 | 8.3 |
| 300 | 5.9 | 8.1 |
| 360[2] | 5.8 | 7.8 |
| 420 | 5.6 | 7.8 |
| 480 | 5.4 | 7.2 |
| 540 | 5.3 | 7.3 |
| 600 | 5.2 | 7.0 |
| 24 hr | 3.4 | 4.9 |

[1]Participants were offered a meal.
[2]Participants were offered a snack.

FIG. 1 is a plot of the semaglutide levels in nmol/L of the control subjects given a Rybelsus™ 7 mg tablet (●) versus the study subjects given the composition of Table 1 times 4 (○). As seen in Table 2 and FIG. 1 the semaglutide levels of the study subjects were consistently 15% higher than the semaglutide levels of the control subjects.

Table I is a summary of the data plotted in FIG. 1 and the observed improvement seen with the composition in Table 1 (test composition).

TABLE I

| Parameter | Test composition | Rybelsus ™ Control | observed improvement | p-value |
|---|---|---|---|---|
| Cmax | 8.8 ng/mL | 6.15 ng/mL | 43% increase | 0.0123 |
| AUC0-t | 154.94 h · ng/mL | 108.69 h · ng/mL | 43% increase | 0.033 |
| AUC0-10 | 71.93 h · ng/mL | 49.0 h · ng/mL | 47% increase | 0.0144 |

Tabulation of geometric least squared mean values comparing Table 1 Composition with semaglutide to Rybelsus ™ semaglutide using a 90% confidence interval
Cmax = Maximum observed concentration
AUC0-t = Area under the curve from 0 time to the last measurable concentration (i.e., the 24 hour mark at the end of the study)
AUC0-10 = Area under the curve from 0 time to the 10 hour point in the study Blood Glucose Levels The Control group evidenced reduced blood glucose levels by between 1.3% and 6.7% relative to the time zero baseline during the first 100 minutes of the Study. The study group evidenced reduced blood glucose levels by between 2.9% and 14.6% relative to baseline during those same initial 100 minutes. At all but the 20 minute and 240-minute sample time points, the study blood glucose levels were reduced more than evidenced by the Control group. It can be seen that even at 24 hours after dose administration, the blood glucose levels were reduced in the study group by 6.3% relative to baseline while the blood glucose level evidenced in the control group was only reduced by 0.67% evidencing nearly a ten-fold improvement with the study group.

These data show that blood glucose levels spiked by up to 22.7% in the control group after the subjects were permitted to eat a standardized meal at the 240-minute mark and a standardized snack at the 360-minute mark. Although the study group subjects consumed choices of similar meals and snacks at the same times, their blood glucose levels rose by up to only 5.3%.

Table 4 shows the glucose blood levels for the subjects in the first leg of the study.

TABLE 4

(all values are in mmol/L)

| Time of draw (min,) | Rybelsus ™ | Study composition |
| --- | --- | --- |
| 0 | 4.97 | 5.15 |
| 20 | 4.90 | 5.00 |
| 40 | 4.90 | 4.65 |
| 60 | 4.63 | 4.53 |
| 80 | 4.70 | 4.48 |
| 100 | 4.70 | 4.40 |
| 120 | 4.53 | 4.40 |
| 140 | 4.70 | 4.43 |
| 160 | 4.80 | 4.40 |
| 180 | 4.47 | 4.43 |
| 210 | 4.70 | 4.45 |
| 240[1] | 4.43 | 4.45 |
| 300 | 5.57 | 4.68 |
| 360[2] | 5.53 | 4.68 |
| 420 | 5.73 | 4.70 |
| 480 | 5.40 | 4.65 |
| 540 | 5.03 | 4.63 |
| 600 | 5.00 | 4.60 |
| 24 hr | 4.93 | 4.83 |

[1]Participants were offered a meal.
[2]Participants were offered a snack.

Figure 4:
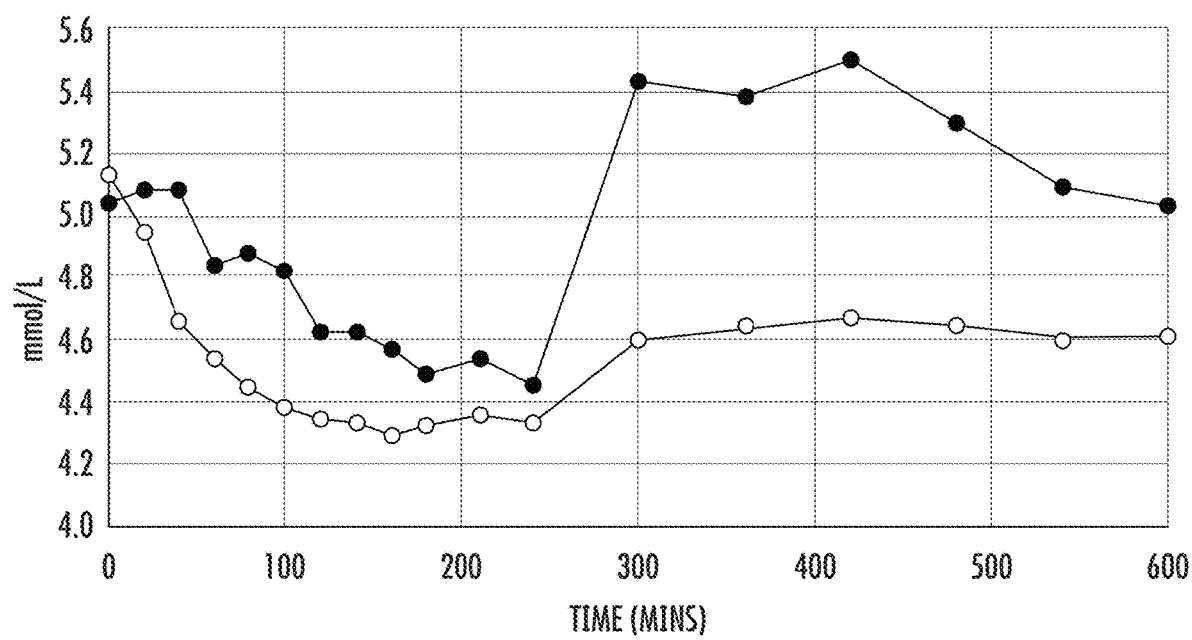
FIG. 4 is a plot of the glucose levels in mmol/L of the combined results (first leg and crossover study) for the subjects administered Rybelsus™ 7 mg tablet (●) versus the combined study subjects given the composition of Table 1 times 4 (○) for an effective amount of semaglutide of 7 mg.

Table 5 below shows glucose blood concentration of the combined data from phase 1 of the study together with the crossover study group (subjects that received Rybelsus™ now receive the composition from Table 1 and vice versus). The combined data from Tables 4 and 5 are depicted in FIG. 4.

TABLE 5

(all values are in mmol/L)

| Time of draw (min,) | Rybelsus ™ | Study composition |
| --- | --- | --- |
| 0 | 4.97 | 5.15 |
| 20 | 4.90 | 5.00 |
| 40 | 4.90 | 4.65 |
| 60 | 4.63 | 4.53 |
| 80 | 4.70 | 4.48 |

TABLE 5-continued (all values are in mmol/L)

| Time of draw (min,) | Rybelsus ™ | Study composition |
| --- | --- | --- |
| 100 | 4.70 | 4.40 |
| 120 | 4.53 | 4.40 |
| 140 | 4.70 | 4.43 |
| 160 | 4.80 | 4.40 |
| 180 | 4.47 | 4.43 |
| 210 | 4.70 | 4.45 |
| 240[1] | 4.43 | 4.45 |
| 300 | 5.57 | 4.68 |
| 360[2] | 5.53 | 4.68 |
| 420 | 5.73 | 4.70 |
| 480 | 5.40 | 4.65 |
| 540 | 5.03 | 4.63 |
| 600 | 5.00 | 4.60 |
| 24 hr | 4.93 | 4.83 |

[1]Participants were offered a meal.
[2]Participants were offered a snack.

Figure 2:
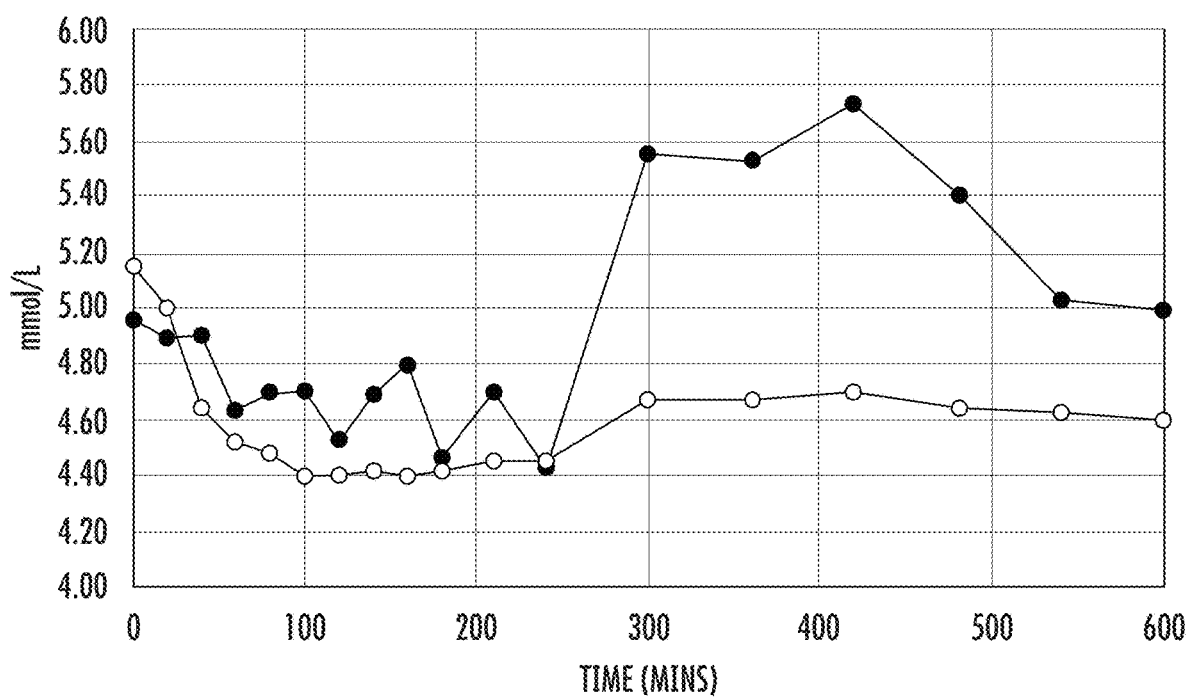
FIG. 2 is a plot of the glucose levels in mmol/L of the control subjects given a Rybelsus™ 7 mg tablet (●) versus the study subjects given the composition of Table 1 times 4 (○).

FIG. 2 is a plot of the glucose levels in mmol/L of the control subjects given a Rybelsus™ 7 mg tablet (●) versus the study subjects given the composition of Table 1 times 4 (○). As seen in Table 3 and FIG. 2 the glucose blood levels of the study subjects was suppressed after a meal at 240 minutes and a snack at 360 minutes.

Semaglutide Levels Study 1 Crossover

Blood was examined by a third-party laboratory using a validated bioassay 18 times over the first 10 hours of the Study, and once again 24 hours after the dose was administered. Each subject fasted for 12 hours prior to testing. Subjects were supervised and monitored in the Study site over the entire 10-hour duration post dosing, and then allowed to depart, resume normal activities and return to the Study site the following day for performance of the 24-hour evaluation time point. The first post-baseline blood was sampled 20 minutes after oral administration and, at that point in time, the study group blood semaglutide level was ~125% higher than that of the Control. At each of the 19 blood sample time points, the study group blood semaglutide levels were higher than the Control levels. Furthermore, the study group peak was achieved faster at 120 minutes (as compared to 160 minutes for the Control) and with a 16% higher blood semaglutide level than the Control. The blood semaglutide levels achieved with the Control were proportional to those achieved in similar single dose cross-over Rybelsus™ development informing studies, further suggesting that the blood semaglutide level gains evidenced by the study group formulation were notably distinct relative to the commercial product. A final blood draw was taken 24 hours after the beginning of testing. Subjects were allowed to return to their normal schedule prior to the 24 hour final blood draw.

FIG. 3 is a plot of the semaglutide levels in nmol/L of the combined results (first leg and crossover study) for the subjects administered Rybelsus™ 7 mg tablet (●) versus the combined study subjects given the composition of Table 1 times 4 (○) for an effective amount of semaglutide of 7 mg. As seen in FIG. 3 the peak levels of semaglutide in blood were 43% higher in the volunteers receiving the composition from Table 1 than in the Rybelsus™ Control, with a value of 8.80 nmol/mL compared to 6.15 nmol/mL respectively (p=0.0123). Furthermore, over the 10 hour duration the subjects were studied in the clinic, for the AUC0-10 (area under the curve from 0 to 10 hours), the geometric least squared mean value from the composition of Table 1 was 47% higher than when Rybelsus™ was administered alone with a value of 71.93 h·nmol/mL compared to 49.00 h·nm/mL respectively (p=0.0114).

FIG. 4 is a plot of the glucose levels in mmol/L of the combined results (first leg and crossover study) for the subjects administered Rybelsus™ 7 mg tablet (●) versus the combined study subjects given the composition of Table 1 times 4 (○) for an effective amount of semaglutide of 7 mg. As seen in FIG. 4 the Control group (7 mg Rybelsus™) evidenced inconsistent blood glucose reduction that did not prevent blood glucose spikes after eating. The volunteers receiving the composition from Table 1 had reduced blood glucose to lower levels and was much more effective at maintaining consistently reduced blood glucose levels even after eating a standardized meal at the 240-minute mark and a standardized snack at the 360-minute mark.

Animal Study 2

Rybelsus™ is the only semaglutide-containing composition approved for oral delivery in humans. Without wishing to be limited by theory, it is believed that the presence of the carrier salcaproate sodium (SNAC) is a critical permeation enhancer which allows for oral delivery of semaglutide. The present disclosure provides animal testing of the disclosed compositions versus Rybelsus™ which serves as the prior art control:
1. A reformulated Rybelsus™ OTC formulation; Tables 9-11.
2. A reformulated Rybelsus™ OTC based on the disclosed compositions; Tables 12-14.
3. A disclosed formulation comprising semaglutide; Tables 15-17.
4. A disclosed formulation comprising liraglutide; Tables 18-20.

The following is a summary of the compositions tested in the four cohorts of Animal Test 2.

Rybelsus™ is used as the prior art control as depicted in Tables 6-8. The prior art control animals are dosed with Rybelsus™ tablets containing 14 mg of semaglutide. Each tablet has a mass of approximately 306 mg.

The Cohort 1 compositions tested below comprise semaglutide obtained from crushed Rybelsus™ tablets which comprise salcaproate sodium carried over into the test composition. Cohort 1 further comprise ox bile salt containing from 45% to 55% by weight of an admixture of cholic acid, deoxycholic acid, taurocholate and glycocholic acid as an adjunct bile salt material.

The Cohort 2 compositions tested below comprise semaglutide obtained from crushed Rybelsus™ tablets which comprise salcaproate sodium carried over into the test composition. Cohort 2 further comprise ox bile salt containing from 45% to 55% by weight of an admixture of cholic acid, deoxycholic acid, taurocholate and glycocholic acid as an adjunct bile salt material. Cohort 2 has a ratio of semaglutide to olive oil of 1:2.

The Cohort 3 compositions comprise semaglutide in a disclosed composition.

The Cohort 4 compositions comprise liraglutide in a disclosed composition.

Prior Art Control-Rybelsus™

TABLE 6

FIRST LEG

Month 1 (0.5 mg/kg)

Sufficient Rybelsus ™ is administered to the animals to achieve the indicated amount of semaglutide per dose. Each Rybelsus tablet contains 14 mg of semaglutide.

Prior Art Control-Rybelsus™

TABLE 7

SECOND LEG

Month 2 (0.75 mg/kg)

Sufficient Rybelsus ™ is administered to the animals to achieve the indicated amount of semaglutide per dose. Each Rybelsus ™ tablet contains 14 mg of semaglutide.

Prior Art Control-Rybelsus™

TABLE 8

THIRD LEG

Month 3 (3 mg/kg)

Sufficient Rybelsus ™ is administered to the animals to achieve the indicated amount of semaglutide per dose. Each Rybelsus ™ tablet contains 14 mg of semaglutide.

Cohort 1: A Reformulated Rybelsus OTC Formulation

TABLE 9

FIRST LEG
Month 1 (0.5 mg/kg)

| Ingredients | Amount per dose (% w/w) | Amount per dose (mg) | Quantity per batch (mg) |
|---|---|---|---|
| Semaglutide[1] | 11 | 5.88 | 2624.83 |
| sunflower oil | 11 | 5.88 | 2624.83 |
| Gum Arabic | 20 | 10.69 | 4772.42 |
| Aeroperl ™ 300 | 20 | 10.69 | 4772.42 |
| Ox bile[2] | 20.82 | 11.13 | 4968.09 |
| Sodium bicarbonate | 17.17 | 9.18 | 4097.12 |
| total | 100 | 53.45 | 19762.60 |

[1]Crushed Rybelsus ™ tablets
[2]contains 45-55% by weight of cholic acid, deoxycholic acid, taurocholate and glycocholic acid

TABLE 10

SECOND LEG
Month 2 (0.75 mg/kg)

| Ingredients | Amount per dose (% w/w) | Amount per dose (mg) | Quantity per batch (mg) |
|---|---|---|---|
| Semaglutide[1] | 11 | 8.82 | 3937.25 |
| sunflower oil | 11 | 8.82 | 3937.25 |
| Gum Arabic | 20 | 16.04 | 7158.63 |
| Aeroperl ™ 300 | 20 | 16.04 | 7158.63 |
| Ox bile[2] | 20.82 | 16.69 | 7452.14 |
| Sodium bicarbonate | 17.17 | 13.77 | 6145.69 |
| total | 100 | 80.18 | 29643.90 |

[1]Crushed Rybelsus ™ tablets
[2]contains 45-55% by weight of cholic acid, deoxycholic acid, taurocholate and glycocholic acid

TABLE 11

THIRD LEG
Month 3 (3 mg/kg)

| Ingredients | Amount per dose (% w/w) | Amount per dose (mg) | Quantity per batch (mg) |
|---|---|---|---|
| Semaglutide[1] | 11 | 35.29 | 15753.46 |
| sunflower oil | 11 | 35.29 | 15753.46 |
| Gum Arabic | 20 | 64.16 | 28642.65 |
| Aeroperl ™ 300 | 20 | 64.16 | 28642.65 |
| Ox bile[2] | 20.82 | 66.79 | 29817.00 |
| Sodium bicarbonate | 17.17 | 55.08 | 24589.71 |
| total | 100 | 320.82 | 118609.20 |

[1]Crushed Rybelsus ™ tablets.
[2]contains 45-55% by weight of cholic acid, deoxycholic acid, taurocholate and glycocholic acid.

Cohort 2: Reformulated Rybelsus OTC Formulation Based Upon the Disclosed Compositions

TABLE 12

FIRST LEG
Month 1 (0.5 mg/kg)

| Ingredients | Amount per dose (% w/w) | Amount per dose (mg) | Quantity per batch (mg) |
|---|---|---|---|
| Semaglutide[1] | 11 | 5.88 | 1640.80 |
| olive oil | 22 | 11.76 | 3281.91 |
| Gum Arabic | 26.925 | 14.40 | 4016.61 |
| Aeroperl ™ 300 | 32.28 | 17.26 | 4815.46 |
| Deoxycholic acid | 0.0745 | 0.04 | 11.11 |
| Sodium bicarbonate | 7.73 | 4.13 | 1153.14 |
| total | 100.0095 | 53.47 | 13765.89 |

[1]Crushed Rybelsus ™ tablets

TABLE 13

SECOND LEG
Month 2 (0.75 mg/kg)

| Ingredients | Amount per dose (% w/w) | Amount per dose (mg) | Quantity per batch (mg) |
|---|---|---|---|
| Semaglutide[1] | 11 | 8.82 | 2461.34 |
| olive oil | 22 | 17.65 | 4923.14 |
| Gum Arabic | 26.925 | 21.60 | 6025.26 |
| Aeroperl ™ 300 | 32.28 | 25.89 | 7223.59 |
| Deoxycholic acid | 0.0745 | 0.06 | 16.67 |
| Sodium bicarbonate | 7.73 | 6.20 | 1729.81 |
| total | 100.0095 | 80.21 | 2461.34 |

[1]Crushed Rybelsus ™ tablets.

TABLE 14

THIRD LEG
Month 3 (3 mg/kg)

| Ingredients | Amount per dose (% w/w) | Amount per dose (mg) | Quantity per batch (mg) |
|---|---|---|---|
| Semaglutide[1] | 11 | 35.29 | 9845.63 |
| olive oil | 22 | 70.58 | 19693.13 |
| Gum Arabic | 26.925 | 86.39 | 24101.71 |
| Aeroperl ™ 300 | 32.28 | 103.57 | 28895.20 |
| Deoxycholic acid | 0.0745 | 0.24 | 66.69 |
| Sodium bicarbonate | 7.73 | 24.80 | 6919.45 |
| total | 100.0095 | 320.84 | 82602.36 |

[1]Crushed Rybelsus ™ tablets

Cohort 3: Disclosed Composition Comprising Semaglutide

TABLE 15

FIRST LEG
Month 1 (0.5 mg/kg)

| Ingredients | Amount per dose (% w/w) | Amount per dose (mg) | Quantity per batch (mg) |
|---|---|---|---|
| Semaglutide | 2.2 | 0.20 | 89.28 |
| olive oil | 4.4 | 0.40 | 178.56 |
| Aeroperl ™ 300 | 25.36 | 2.31 | 1029.154909 |
| Parteck ™ M 100 | 22.2 | 2.02 | 900.9163636 |
| Deoxycholic acid | 0.44 | 0.04 | 17.856 |
| Sodium bicarbonate | 45.4 | 4.13 | 1842.414545 |
| total | 100 | 9.09 | 4058.18 |

TABLE 16

SECOND LEG
Month 2 (0.75 mg/kg)

| Ingredients | Amount per dose (% w/w) | Amount per dose (mg) | Quantity per batch (mg) |
|---|---|---|---|
| Semaglutide | 2.2 | 0.30 | 133.92 |
| olive oil | 4.4 | 0.60 | 267.84 |
| Aeroperl ™ 300 | 25.36 | 3.46 | 1543.732 |
| Parteck ™ M 100 | 22.2 | 3.03 | 1351.375 |
| Deoxycholic acid | 0.44 | 0.06 | 26.784 |
| Sodium bicarbonate | 45.4 | 6.19 | 2763.622 |
| total | 100 | 13.64 | 6087.27 |

TABLE 17

THIRD LEG
Month 3 (3 mg/kg)

| Ingredients | Amount per dose (% w/w) | Amount per dose (mg) | Quantity per batch (mg) |
|---|---|---|---|
| Semaglutide | 2.2 | 1.20 | 535.68 |
| olive oil | 4.4 | 2.40 | 1071.36 |
| Aeroperl ™ 300 | 25.36 | 13.83 | 6174.929 |
| Parteck ™ M 100 | 22.2 | 12.11 | 5405.498 |
| Deoxycholic acid | 0.44 | 0.24 | 107.136 |
| Sodium bicarbonate | 45.4 | 24.76 | 11054.49 |
| total | 100 | 54.55 | 24349.09 |

Cohort 4: Disclosed Composition Comprising Liraglutide

TABLE 18

FIRST LEG
Month 1 (0.5 mg/kg)

| Ingredients | Amount per dose (% w/w) | Amount per dose (mg) | Quantity per batch (mg) |
|---|---|---|---|
| liraglutide | 2.2 | 0.20 | 89.28 |
| olive oil | 4.4 | 0.40 | 178.56 |
| Aeroperl ™ 300 | 25.36 | 2.31 | 1029.154909 |
| Parteck ™ M 100 | 22.2 | 2.02 | 900.9163636 |
| Deoxycholic acid | 0.44 | 0.04 | 17.856 |
| Sodium bicarbonate | 45.4 | 4.13 | 1842.414545 |
| total | 100 | 9.09 | 4058.18 |

TABLE 19

SECOND LEG
Month 2 (0.75 mg/kg)

| Ingredients | Amount per dose (% w/w) | Amount per dose (mg) | Quantity per batch (mg) |
|---|---|---|---|
| liraglutide | 2.2 | 0.30 | 133.92 |
| olive oil | 4.4 | 0.60 | 267.84 |
| Aeroperl ™ 300 | 25.36 | 3.46 | 1543.732 |
| Parteck ™ M 100 | 22.2 | 3.03 | 1351.375 |
| Deoxycholic acid | 0.44 | 0.06 | 26.784 |
| Sodium bicarbonate | 45.4 | 6.19 | 2763.622 |
| total | 100 | 13.64 | 6087.27 |

TABLE 20

THIRD LEG
Month 3 (3 mg/kg)

| Ingredients | Amount per dose (% w/w) | Amount per dose (mg) | Quantity per batch (mg) |
|---|---|---|---|
| liraglutide | 2.2 | 1.20 | 535.68 |
| olive oil | 4.4 | 2.40 | 1071.36 |
| Aeroperl ™ 300 | 25.36 | 13.83 | 6174.929 |
| Parteck ™ M 100 | 22.2 | 12.11 | 5405.498 |
| Deoxycholic acid | 0.44 | 0.24 | 107.136 |
| Sodium bicarbonate | 45.4 | 24.76 | 11054.49 |
| total | 100 | 54.55 | 24349.09 |

Animal Study 2 Design

The following is an outline of the Animal Study 2 Design

TABLE 21

| Study Day | Event | Procedure |
|---|---|---|
| −3 | Animals arrive | Animals arrive at test facility |
| 0-14 | Validation Phase | Daily body weights and observations<br>Blood glucose measurement (Day 6, 12)<br>Day 14: Group allocation based on body weight and blood glucose levels from Day 12 |
| 15-42 | Treatment Phase 1 | Daily body weights and observations<br>Daily drug administration of Dose 1 for 28 consecutive days (12 Study groups)<br>Blood glucose measurement (Day 21, 28, 42)<br>Day 15, 42: Blood collection (1, 4, 24 hr after first treatment, pre, 1, 4, 24 hr following final treatment) |
| 44-71 | Treatment Phase 2 | Daily body weights and observations<br>Daily drug administration of Dose 2 for 28 consecutive days (12 Study groups)<br>Blood glucose measurement (Day 50, 57, 71)<br>Day 44, 71: Blood collection (1, 4, 24 hr after first treatment, pre, 1, 4, 24 hr following final treatment)<br>Terminal collections (If Treatment Phase 3 not run) |
| 73-101 | Treatment Phase 3 | Daily body weights and observations<br>Daily drug administration of Dose 3 for 28 consecutive days (12 Study groups)<br>Blood glucose measurement (Day 79, 86, 101)<br>Day 73, 101: Blood collection (1, 4, 24 hr after first treatment, pre, 1, 4, 24 hr following final treatment)<br>Terminal collections (If Treatment Phase 3 run) |

Study Procedures

Housing and Acclimation

Seventy-two (72) male Zucker obese rats (ZDF fa/fa, CRL strain code 370), 3 months of age from Charles River Laboratories served as test subjects in this study. The Zucker obese rats are specifically bred with a pair of recessive fatty genes (fa/fa). The animals were acclimatized to their new environment for a minimum of 3 days prior to testing. Subjects were maintained on a 12 h/12 h light/dark cycle with all experimental activity occurring during the animals' light cycle.

Food and Water

Purina LabDiet® 5008 was provided ad libitum to all study subjects. Water was provided ad libitum in glass bottles with stainless steel sippers. The Control group was only given water during the test period.

Treatment Groups

This study was performed on 24 Zucker obese rats.

TABLE 22

| Cohort | Treatment | N | Route |
|---|---|---|---|
|  | Control | 6 | PO |
|  | Positive Control - Rybelsus ™ | 6 | PO |
| 1 | Reformulated Rybelsus ™ OTC formulation | 6 | PO |
| 2 | Reformulated Rybelsus ™ OTC per disclosed compositions | 6 | PO |
| 3 | Disclosed formulation comprising semaglutide | 6 | PO |
| 4 | Disclosed formulation comprising liraglutide | 6 | PO |

Validation Phase

The validation phase spans from Study Day 0 to Study Day 14. Animals were maintained on LabDiet 5008 throughout the course of the study.

Blood Glucose Measures

Blood glucose was measured on Study Days 6 and 12 by puncturing the saphenous vein for 1 drop of blood measured via Accu-Chek glucose monitor.

Group Allocation

On Study Day 14, the animals were allocated into 1 of 4 treatment groups, balanced by body weight and blood glucose from Study Day 12.

Treatment Phase

There are three (3) treatment phases in this study. Treatment phase 1 spans from Study Day 15 to Study Day 42. A one-day washout period occurs between each treatment phase to facilitate a decision-making process regarding subsequent doses in the subsequent treatment phase. Treatment phase 2 occurs on study Days 44 to 71. Treatment phase 3 will occur on study Days 73 to 101. The decision to run Treatment 3 is based on a Go/NoGo decision after reviewing data from Treatment 1 and 2.

Test Article Administration

Once daily, animals are administered their respective treatment of test article, Rybelsus™ or vehicle for 28 consecutive days. Test article and Rybelsus™ were administered in the late afternoon close to the animals natural feeding time.

Blood Collection and Analysis

Blood is collected (0.3 mL) on the first and last day of each treatment phase via sampling from the saphenous vein into K2EDTA blood collection tubes for plasma isolation. Blood is collected at 1, 4, 24 hours post dose on the first dosing day, and pre-dose, 1, 4, 24 hours post-dose on the last dosing day of each treatment cycle. Blood glucose was measured upon first puncture via Accu-Chek glucose monitor. Samples were centrifuged to isolate for plasma (3200 RCF for 5 minutes at 4° C. and shipped to an external bioanalytical lab for analysis. Blood glucose is measured on days 7, 14, and 28 of each treatment phase by puncturing the saphenous vein for 1 drop of blood measured via Accu-Chek glucose monitor.

The following Tables list the change in animal mass for Cohorts 1-4 over the 84 day test period.

TABLE 23

| | Animal mass (g) | | | | | | |
|---|---|---|---|---|---|---|---|
| Cohort | Animal mass (g) at Acclimation | Day 28 mass (g) | % mass Change at Day 28 | Day 56 mass (g) | % mass Change at Day 56 | Day 84 mass (g) | % mass Change at Day 84 |
| Control | 427.7 | 442.5 | +3.46% | 440.1 | +2.90% | 433.7 | +1.40% |
| Rybelsus | 430.2 | 446.7 | +3.84% | 459.2 | +6.74% | 454.5 | +5.65% |
| 1 | 394.9 | 394.6 | −0.06% | 401.4 | +1.65% | 393.6 | −0.32% |
| 2 | 406.2 | 409.1 | +0.70% | 406.7 | +0.11% | 403.1 | −0.78% |
| 3 | 394.2 | 394.8 | +0.15% | 399.0 | +1.21% | 394.1 | −0.02% |
| 4 | 392.2 | 385.7 | −1.65% | 373.6 | −4.74% | 369.1 | −5.88% |

The following Table lists the change in animal blood sugar levels (mmol/L) for Cohorts 1-4 over the 84 day test period.

TABLE 24

| | Blood Sugar Levels (mmol/L) | | | | | | |
|---|---|---|---|---|---|---|---|
| Cohort | Animal at Acclimation | Day 28 | Change Day 28 | Day 56 | Change Day 56 | Day 84 | Change Day 84 |
| Control | 24.2 | 25.7 | 6.2% | 27.7 | 14.46% | 26.7 | 10.33% |
| Rybelsus | 24.3 | 25.1 | 3.29% | 26.1 | 7.41% | 24.2 | −0.41% |
| 1 | 26.4 | 25.5 | −3.60% | 26.8 | 1.33% | 26.8 | 1.59% |
| 2 | 24.9 | 26.8 | 7.70% | 26.4 | 5.96% | 27.3 | 9.58% |
| 3 | 26.3 | 25.9 | −1.52% | 27.8 | 5.54% | 26.9 | 2.13% |
| 4 | 26.4 | 25.8 | −2.08% | 25.2 | −4.56% | 23.3 | −11.54% |

As evidenced by the data in Tables 23 and 24 the compositions disclosed herein are capable of delivering semaglutide and liraglutide to the blood plasma of test animals and thereby affecting body mass as well as blood glucose levels in the absence of sodium N-[8-(2-hydroxybenzoyl)amino]caprylate (SNAC). Of note, each of the compositions disclosed herein achieved better body weight control than the Rybelsus™ positive control group. At Day 84, compared to the Rybelsus™ positive control group, Cohort 1 showed an improvement of 5.97% (p=0.0016); Cohort 2 showed an improvement of 6.43% (p<0.0001);

Cohort 3 showed an improvement of 5.67% (p=0.0007); and Cohort 4 showed an improvement of 11.53% (p<0.0001).

Other advantages which are obvious and which are inherent to the disclosure will be evident to one skilled in the art. It will be understood that certain features and sub-combinations are of utility and can be employed without reference to other features and sub-combinations. This is contemplated by and is within the scope of the claims. Since many possible embodiments can be made relating to this disclosure without departing from the scope thereof, it is to be understood that all matter herein set forth or shown in the accompanying drawings is to be interpreted as illustrative and not in a limiting sense.

What is claimed is:

1. A composition, consisting of:
   a) from about 0.5% to about 20% by weight of one or more glucagon-like peptide-1 (GLP-1) agonists;
   b) from about 0.5% to about 40% by weight of olive oil;
   c) from about 1.5% to about 65% by weight of a bile salt extract;
   d) from about 35% to about 65% by weight of sodium bicarbonate; and
   from about 15% to about 85% by weight of one or more carriers chosen from mannitol, and colloidal silicon dioxide, or mixtures thereof.

2. The composition according to claim 1, wherein the GLP-1 agonist is chosen from dulaglutide, exenatide, lixisenatide, semaglutide, and tirzepatide, or mixtures thereof.

3. The composition according to claim 1, wherein the GLP-1 agonist is semaglutide.

4. The composition according to claim 1, wherein the bile salt extract contains from about 45% to about 55% by weight of a bile salt selected from the group consisting of cholic acid, deoxycholic acid, taurocholate, and glycocholic acid, or a mixture thereof.

5. The composition according to claim 1, wherein the bile salt is deoxycholic acid.

6. A composition, consisting of:
   a) from about 0.2 mg to about 25 mg of one or more GLP-1 agonists chosen from dulaglutide, exenatide, lixisenatide, semaglutide, and tirzepatide, or mixtures thereof;
   b) from about 0.4 mg to about 50 mg of olive oil;
   c) from about 0.05 mg to about 5 mg of a bile salt extract wherein the bile salts are an extract containing from about 45% to about 55% by weight of cholic acid, deoxycholic acid, taurocholate, and glycocholic acid, or mixtures thereof;
   d) from about 1 mg to about 460 mg of sodium bicarbonate; and
   e) from about 3 mg to about 480 mg of one or more carriers chosen from mannitol, colloidal silicon dioxide, or mixtures thereof.

7. The composition according to claim 6, wherein the GLP-1 agonist is semaglutide.

8. The composition according to claim 6, wherein the bile salt is deoxycholic acid.

9. A method for treating type-2 diabetes in a subject comprising administering to a subject in need a composition consisting of:
   a) from about 0.2 mg to about 25 mg of one or more GLP-1 agonists chosen from dulaglutide, exenatide, lixisenatide, semaglutide, and tirzepatide, or mixtures thereof,
   b) from about 0.4 mg to about 50 mg of olive oil;
   c) from about 0.05 mg to about 5 mg of a bile salt extract wherein the bile salts are an extract containing from about 45% to about 55% by weight of cholic acid, deoxycholic acid, taurocholate, and glycocholic acid, or mixtures thereof;
   d) from about 1 mg to about 460 mg of sodium bicarbonate; and
   e) from about 3 mg to about 480 mg of one or more carriers chosen from mannitol, colloidal silicon dioxide, or mixtures thereof.

10. The method according to claim 9, wherein the GLP-1 agonist is semaglutide.

11. The method according to claim 9, wherein the bile salt is deoxycholic acid.

* * * * *